US007186530B1

(12) United States Patent
Wei et al.

(10) Patent No.: US 7,186,530 B1
(45) Date of Patent: Mar. 6, 2007

(54) PROTEIN ASSOCIATED WITH CELL STRESS RESPONSE

(75) Inventors: Dong Wei, San Francisco, CA (US); Robert F. Halenbeck, San Rafael, CA (US); Lewis T. Williams, Mill Valley, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/544,776

(22) Filed: Apr. 7, 2000

(51) Int. Cl.
| | |
|---|---|
| C12Q 1/68 | (2006.01) |
| C12P 12/04 | (2006.01) |
| C12P 19/34 | (2006.01) |
| C12N 15/00 | (2006.01) |
| C07H 21/04 | (2006.01) |

(52) U.S. Cl. .................. 435/70.1; 435/6; 435/91.1; 435/91.31; 435/320.1; 435/455; 536/23.1; 536/24.5

(58) Field of Classification Search .............. 435/6, 435/91.1, 455, 375, 70.1, 91.31, 320.1, 458; 514/44; 536/23.1, 24.5
See application file for complete search history.

(56) References Cited

U.S. PATENT DOCUMENTS 5,858,708 A * 1/1999 Bandman et al. ........... 435/69.1

FOREIGN PATENT DOCUMENTS

| WO | WO 93/00427 | | 1/1993 |
| WO | WO 98/06841 | * | 2/1998 |
| WO | WO 00/05364 | | 2/2000 |
| WO | WO 00/31235 | | 6/2000 |
| WO | WO 01/36631 | * | 5/2001 |

OTHER PUBLICATIONS

Theodore Friedmann, Overcoming the Obstacles to Gene Therapy, Scientific American, pp. 96-101, Jun. 1997.*
Giorgio Palu et al., In pursuit of new developments for gene therapy of human diseases, Journal of Biotechnology, 68, pp. 1-13, 1999.*
Inder M. Verma et al., Gene therapy—promises, problems, and prospects, Nature, vol. 389 pp. 239-242 Sep. 18, 1997.*
Andrea D. Branch, A good antisense molecule is hard to find, TIBS 23, pp. 45-50, Feb. 1998.*
Ronald G. Crystal, Transfer of Genes to Humans: Early Lessons and Obstacles to Success, Science, vol. 270 pp. 404-410, 1995.*
W. James, Towards gene—inhibition therapy: a review of progress and prospects in the field of antiviral antisense nucleic acids and ribozymes, Antiviral Chemistry & Chemotherapy, 2(4). pp. 191-214, 1991.*
Natalie Milner et al., Selecting effective antisense reagents on combinatorial oligonucleotide arrays, Nature Biotechnology, vol. 15, pp. 537-541, Jun. 1997.*
J. P. Schofield et al., Non-viral approaches to gene therapy, British Medical Bulletin, vol. 51, No. 1, pp. 56-71, 1995.*
Stanley T. Crooke, Basic Principles of Antisense Therapeutic, pp. 1-50.*
Bowie et al., "Deciphering the message in protein sequences: tolerance to amino acid substitutions," Science 247(4948):1306-1310, Mar. 1990.
Chen et al., "Nogo-A is a myelin-associated neurite outgrowth inhibitor and an antigen for monoclonal antibody IN-1," Nature, 403:434-439, Jan. 27, 2000.
Chen et al., "Neurite outgrowth inhibitory factors in CNS myelin: molecular characterization of Nogo (NI-35/250)," Society for Neuroscience Abstracts 24:1766, 1998.
Cremers et al., "Mapping and cloning hereditary deafness genes," Current Opinion in Genetics and Development 5:371-375, Jun. 1995.
Cunningham and Wells, "High-resolution epitope mapping of hGH-receptor interactions by alanine-scanning mutagenesis," Science 244(4908):1081-1085, Jun. 1989.
Davies et al., "Robust regeneration of adult sensory axons in degenerating white matter of the adult rat spinal cord," The Journal of Neuroscience 19(14):5810-5822, Jul. 1999.
Goldberg and Barres, "Nogo in nerve regeneration," Nature, 403:369-370, Jan. 27, 2000.
GrandPre et al., "Identification of the Nogo inhibitor of axon regeneration as a Reticulon protein," Nature, 403:439-444, Jan. 27, 2000.
Leppa and Sistonen, "Heat shock response—pathophysiological implications," Annals of Medicine 29:73-78, 1997.
Lian-Jun et al., "Bardet-Biedl syndrome: a review of Chinese literature and a report of two cases," Ophthalmic Genetics 19(2):107-109, Jun. 1998.
Morimoto and Santoro, "Stress-inducible responses and heat shock proteins: a new pharmacologic targets for cytoprotection," Nature Biology 16:833-838, Sep. 1998.
Ozer et al., "Clinical features of Bardet-Biedl syndrome," Acta Paediatrica Japonica 37:233-236, 1995.
Paschen and Doutheil, "Disturbances of the functioning of endoplasmic reticulum: a key mechanism underlying neuronal cell injury?" Journal of Cerebral Blood Flow and Metabolism 19:1-18, Jan. 1999.
Prinjha et al., "Inhibitor of neurite outgrowth in humans," Nature, 403:383-384, Jan. 27, 2000.
Punyiczki and Fesus, "Heat shock and apoptosis," Annals of the New York Academy of Sciences 851:67-74, Jun. 30, 1998.
Rokutan et al., "Implications of heat shock / stress proteins for medicine and disease," The Journal of Medical Investigation 44:137-147, Feb. 1998.
van Aarem et al., "Usher Syndrome. A temporal bone report," Archives of Otolaryngology Head and Neck Surgery 121(8):916-921, Aug. 1995.
Wong and Wispe, "The stress response and the lung," The American Physiological Society 17(1):L1-L9, Jul. 1997.
Wong, H., "Potential protective role of heat shock response in sepsis," New Horizons 6(2):194-200, May 1998.

* cited by examiner

Primary Examiner—Jane Zara
(74) Attorney, Agent, or Firm—Lisa E. Alexander; Gwilym Attwell; Alisa A. Harbin

(57) ABSTRACT

A stress-phosphorylated endoplasmic reticulum protein, Nogo B, is provided. The protein is hyperphosphorylated as a result of exposure of cells to stress. Two transcripts of Nogo B are identified in human tissues, and the longer transcript is predominant in human brain tumor samples.

15 Claims, 12 Drawing Sheets

```
  1  MEDLDQSPLV SSSDSPPRPQ PAFKYQFVRE PEDEEEEEEE EEEDEDEDLE
 51  ELEVLERKPA AGLSAAPVPT APAAGAPLMD FGNDFVPPAP RGPLPAAPPV
101  APERQPSWDP SPVSSTVPAP SPLSAAAVSP SKLPEDDEPP ARPPPPPPAS
151  VSPQAEPVWT PPAPAPAAPP STPAAPKRRG SSGSVVVDLL YWRDIKKTGV
201  VFGASLFLLL SLTVFSIVSV TAYIALALLS VTISFRIYKG VIQAIQKSDE
251  GHPFRAYLES EVAISEELVQ KYSNSALGHV NCTIKELRRL FLVDDLVDSL
301  KFAVLMWVFT YVGALFNGLT LLILALISLF SVPVIYERHQ AQIDHYLGLA
351  NKNVKDAMAK IQAKIPGLKR KAE
```

B.

```
               1                                                      50
NSP-B   MAAEDALPSG YVSFGHVGGP PPSPASPSIQ YSILREEREA ELDSE.....
SPERP   ..MEDLDQSP LVS....SSD SPPRPQPAFK YQFVREPEDE EEEEEEEED
              51                                                     100
NSP-B   .......... LIIESCDASS ASEESPKREQ DSPPMK.... ..PSALDAIR
SPERP   EDEDLEELEV LERKPAAGLS AAPVPTAPAA GAPLMDFGND FVPPAPRGPL
             101                                                     150
NSP-B   EETGVRAEER APSRRGLAEP GSFLDYPSTE PQPGPELPPG DGALEPETPM
SPERP   PAAPPVAPER QPSWDPSPVS STV...PAPS PLSAAAVSPS KLPEDDEPPA
             151                                                     200
NSP-B   LPRKPEEDSS SNQSPAATKG PGPLGPGAPP PLLFLNKQKA ......IDLL
SPERP   RPPPPPPASV SPQAEPVWTP PAP.APAAPP STPAAPKRRG SSGSVVVDLL
             201                                                     250
NSP-B   YWRDIKQTGI VFGSFLLLLF SLTQFSVVSV VAYLALAALS ATISFRIYKS
SPERP   YWRDIKKTGV VFGASLFLLL SLTVFSIVSV TAYIALALLS VTISFRIYKG
             251                                                     300
NSP-B   VLQAVQKTDE GHPFKAYLEL EITLSQEQIQ KYTDCLQFYV NSTLKELRRL
SPERP   VIQAIQKSDE GHPFRAYLES EVAISEELVQ KYSNSALGHV NCTIKELRRL
             301                                                     350
NSP-B   FLVQDLVDSL KFAVLMWLLT YVGALFNGLT LLLMAVVSMF TLPVVYVKHQ
SPERP   FLVDDLVDSL KFAVLMWVFT YVGALFNGLT LLILALISLF SVPVIYERHQ
             351                           383
NSP-B   AQIDQYLGLV RTHINAVVAK IQAKIPGAKR HAE
SPERP   AQIDHYLGLA NKNVKDAMAK IQAKIPGLKR K
```

```
   FLIP
1LtvLsLlPfilimmTSFlKisiVLsllRNALGvQQvPPNmvLyGlA
                    l  +LsL +f ++ +T+++           AL
+L+++
   SPERP      206      LFLLLSLTVFSIVSVTAYI-----------AL---------
ALLSVT 232

FLIP
LfLTlFVMaPvfeeiydrahqplldalsniislqealdkglePlReFmlk
                        + ++iy+ ++q +++              +d+g  P+R
++
   SPERP      233 ----------ISFRIYKGVIQAIQK-----------SDEG-
HPFRAYLES 260

FLIP
htdekh.elalFmrsareerlwPkemkaatlekddLlvLiPAFvlSELkr
                  +    ++++    +sa      +     t++
EL+r
   SPERP      261 EVAISEeLVQKYSNSA-------LGHVNCTIK-------------
ELRR 289

FLIP
AFeIGFLiYLPFiVIDLVVAsiLMAMGMmMvpPvtISLPFKLlLFV....
                             F+V DLV              SL F  l  V
+
   SPERP      290 ----------LFLVDDLVD-----------------
SLKFAVLMWVftyv 312

FLIP             ..LvDGWtLLlggLv
                   + L +G tLL+   L+
   SPERP      313 gaLFNGLTLLILALI     327
```

Figure 6
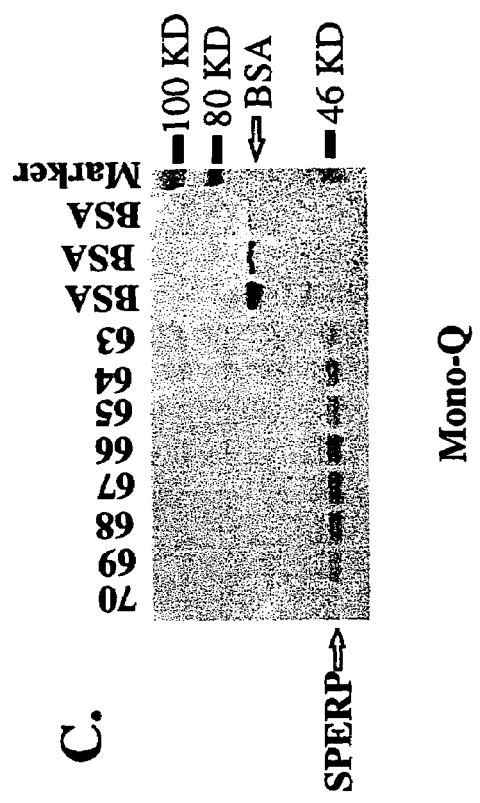
C. Mono-Q
A. Mono-S
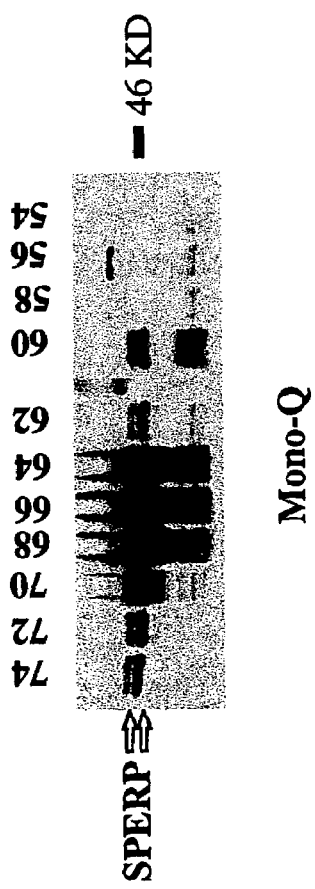
B. Mono-Q

US 7,186,530 B1

PROTEIN ASSOCIATED WITH CELL STRESS RESPONSE

TECHNICAL FIELD

This invention relates to the identification and recombinant expression of a stress-related protein associated with the endoplasmic reticulum.

BACKGROUND OF THE INVENTION

The endoplasmic reticulum (ER) is the site of production of most transmembrane proteins and lipids for cell organelles. The ER captures proteins from the cytosol as they are synthesized, and these proteins are transmembrane proteins or soluble proteins. The soluble proteins are fully translocated across the membrane and released into the ER lumen. In contrast, transmembrane proteins are only partially translocated across the ER membrane. During the course of protein synthesis and processing, the proteins fold to form their tertiary structure.

When cells are exposed to conditions that disrupt protein folding in the ER, the transcription of genes encoding ER proteins may be upregulated. An unfolded protein response (UPR) exists in cells; this response follows detection of unfolded protein in the ER lumen. During the response, a signal is transduced across the ER membrane to activate transcription of selected genes in the nucleus.

Stress and stress responses can have many deleterious effects on an organism. There is a need in the art for additional therapeutic compositions to modulate stress responses.

SUMMARY OF THE INVENTION

The invention provides a new protein that is associated with the endoplasmic reticulum. The protein is hyperphosphorylated in conditions of cell stress.

The invention relates to a native human Nogo protein that is substantially free of other human proteins.

The invention further relates to a protein having the amino acid sequence of SEQ ID NO:2.

The invention still further relates to variants of the protein of SEQ ID NO:2 and to fusion proteins comprising all or part of SEQ ID NO:2.

The invention also relates to polynucleotides encoding all or part of the protein of SEQ ID NO:2.

The invention further relates to a polynucleotide having the sequence of SEQ ID NO:1, and to polynucleotides having at least 85% homology to SEQ ID NO:1.

The invention relates to antibodies, including monoclonal and polyclonal antibodies, that recognize all or part of the Nogo protein of the invention, and to fragments of antibodies including single-chain antibodies.

The invention further relates to methods of identifying the Nogo proteins of the invention using the antibodies.

The invention also relates to methods of identifying or quantifying expression products of the gene encoding the Nogo of the invention, using probes capable of hybridizing to RNA or DNA encoding the Nogo protein, under stringent conditions.

The invention relates to methods of detecting cell stress, wherein the phosphorylation of the protein of the invention is detected or measured.

The invention also relates to methods of modulating phosphorylation of Nogo proteins during stress, using agents that inhibit the phosphorylation of Nogo.

The invention further relates to methods of inactivating a Nogo protein by stimulating phosphorylation of the Nogo protein.

The invention still further relates to methods of inhibiting a Nogo protein using antisense polynucleotides and ribozymes, and to related methods of stimulating cell turnover.

BRIEF DESCRIPTION OF THE DRAWINGS

FIG. 1. The sequence of Nogo. (A) Amino acid sequence of Nogo (SeQ ID No:2) deduced from the DNA sequence of the cDNA in clone 610949. Peptide sequences obtained from the purified Nogo protein via Mass Spectrometry and Microsequencing are underlined. (B) Amino acid sequences of Nogo (SeQ ID No:2) and NSP-B (SeQ ID No:7) were compared using the PILEUP program. Consensus sequences are highlighted. (C) The full-length sequence of Nogo was used for homology searching against the PROSITE database with the PFAMPROT program. FLIP was the only domain with the score above threshold. The score was −150.6, with an E-value of 8.6.

FIG. 4 shows hyperphosphorylation of Nogo after treatment with other stress-inducing agents. (A) IMR90 cells were treated with 0, 0.5, 1, or 4 μM of BPDE and trypsinized after 30 minutes. (B) IMR90 cells were incubated in the presence or absence of suramin (0.15 mM) for 1 hour before being irradiated with 0 or 20 J/m$^2$ of UVC. (C) IMR90 cells were treated with 0.7 M NaCl, 1 mM H$_2$O$_2$, 0.4 M Sorbitol or PBS (control) for 45 minutes before being lysed.

FIG. 5 shows that hyperphosphorylation of Nogo could be abolished by specific inhibitors against p38. IMR90 cells were incubated in the presence of SB202190 and PD169316, two specific inhibitors against p38, at indicated concentrations for 30 minutes. Then cells were irradiated with 20 J/m$^2$ of UVC and lysed 30 minutes later. Whole cell lysates were separated on SDS-PAGE. SC-54 was used for Western Blotting.

FIG. 6. FIG. 6 illustrates the purification of Nogo. (A) Exponentially growing IMR90 cells were lysed by digitonin followed by NP-40 as described in Materials and Methods. Only the NP-40-solubilized fraction was subjected to purification by Mono-S column. Eluted fractions were separated on SDS-PAGE. SC-54 was used for Western Blotting. Positions of Nogo B and the 46 KD protein marker are shown. Fraction numbers were indicated. (B) Eluted fractions 42–48 from the Mono-S column were combined and subjected to purification by Mono-Q column. Eluted fractions were separated on SDS-PAGE. SC-54 was used for Western Blotting. Positions of Nogo and the 46 KD protein marker are shown. Fraction numbers are indicated. (C) Eluted fractions from Mono-Q column were separated on SDS-PAGE. The gel was then stained with Coomassie Bright Blue. Sizes of the molecular weight markers are shown. BSA was loaded as an indicator of size and amount of protein.

FIG. 7 shows hyperphosphorylation of Nogo after UVC irradiation. (A) IMR90 cells were irradiated with 0 or 20 J/m$^2$ of UVC (254 nm). (B) IMR90 cells were synchronized at G1 phase, irradiated with 0 (G1-0) or 20 J/m$^2$ (G1-20) of UVC and trypsinized 2 hours later. (C) IMR90 cells were irradiated with 20 J/m$^2$ of UVC and lysed using buffers with or without vanadate two hours later.

DETAILED DESCRIPTION OF THE INVENTION

Figure 2:
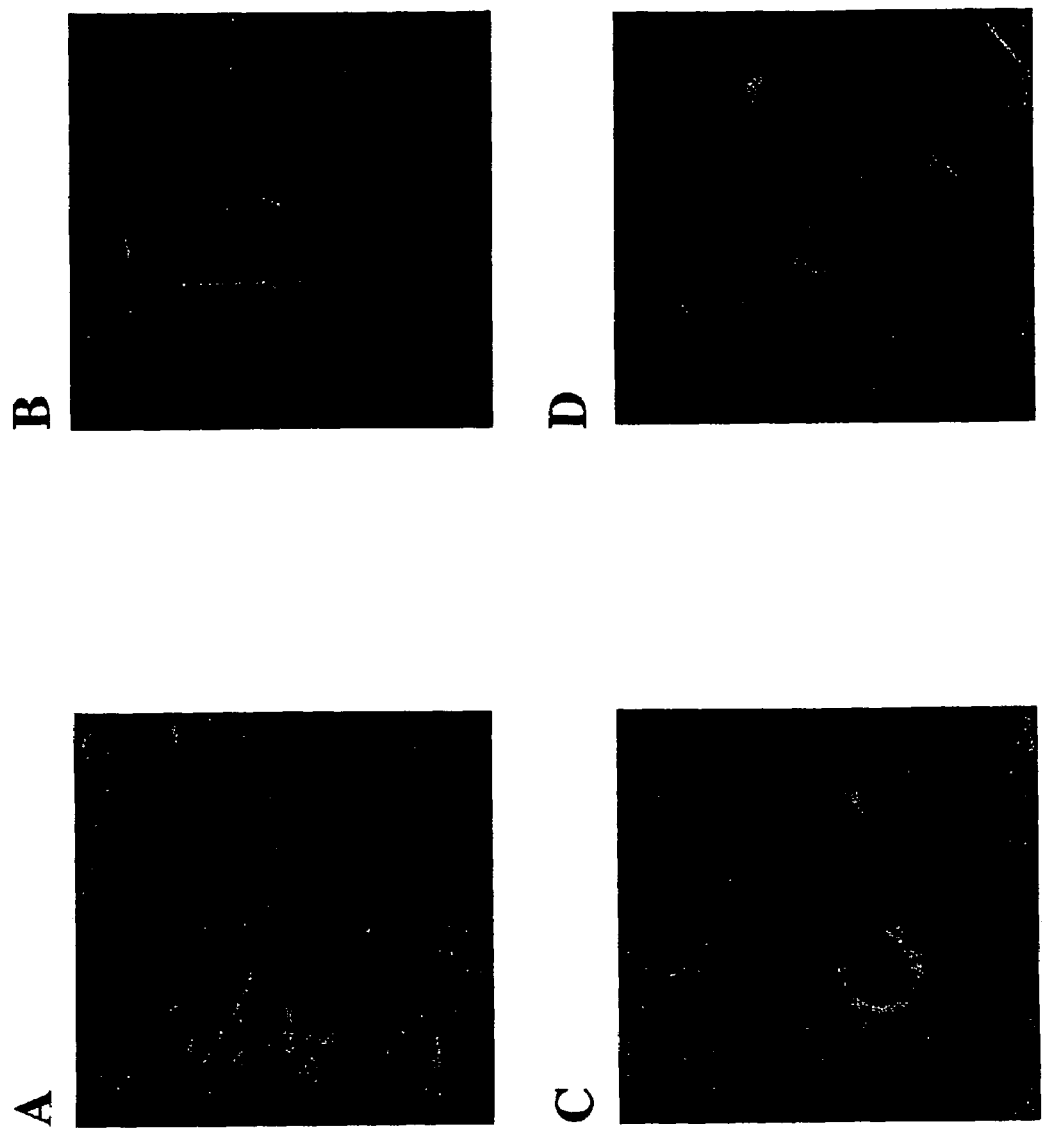
FIG. 2. Subcellular localization of Nogo. IMR90 cells (A,B) or GM00637 cells (C,D) were infected with a retrovirus expressing EGFP alone (A) or an EGFP-Nogo fusion protein (B,C,D). Pictures were taken at 2–3 days after infection. (E). IMR90 cells infected with retrovirus expressing EGFP alone (lanes 1 and 2) or an EGFP-Nogo fusion protein (lanes 3 and 4) were trypsinized and lysed with digitonin followed by NP-40. Digitonin-solubilized fractions (cyto; lanes 1 and 3) and NP-40-solubilized fractions (nuc; lanes 2 and 4) were separated on SDS-PAGE and transferred to a PVDF membrane. A monoclonal antibody against GFP was used for Western Blotting.
Figure 2:
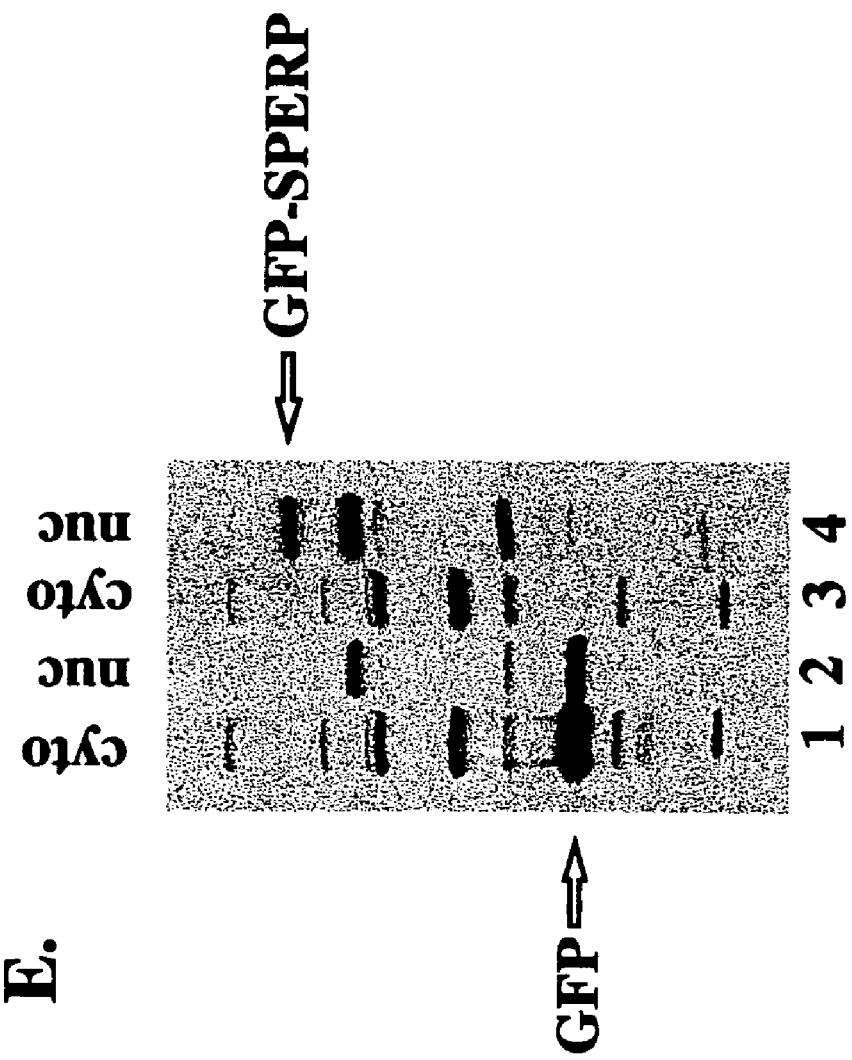

Cells respond to a variety of extracellular stimuli via activation of the mitogen-activated protein (MAP) kinase cascades. The specificity of the cellular response is determined by the activation of a particular MAP kinase pathway in response to a given stimulus and by the activation of downstream targets by a given MAP kinase. P38s are members of the MAP kinase superfamily and they are activated by cell stresses such as DNA damage, heat shock, osmotic shock, as well as proinflammatory stimuli such as lipopolysaccharides and interleukin-1. There are four members in the p38 family: p38α (also known as SAPK2a, RK, CSBP), p38β (SAPK2b), p38γ (SAPK3) and p38σ (SAPK4). All four are activated by MAP kinase kinase (MKK) 3 or MKK6 via phosphorylation of the TGY motif. How MKK3 or MKK6 are regulated is poorly understood. It has been shown that activation of the kinase cascade leading to stimulation of p38 requires the Rho-subfamily GTPases Cdc42 and Rac. The MLK3 family of protein kinases has been shown to be activators of MKK3 and MKK6, but there are likely to be others.

Identified substrates for p38s include transcription factors and protein kinases such as ribosomal S6 kinase (RSK; also known as MAPKAP-K1), MAP kinase-interacting kinases or MAP kinase-integrating kinase (MNK), p38 regulated/activated kinase (PRAK) and MAP kinase activated protein kinases (MAPKAP-Ks). RSK proteins have been shown to play important roles in a variety of processes including cell proliferation. MNK can phosphorylate eukaryotic initiation factor-4E (eIF-4E) in vitro, suggesting an important link between MAP kinase activation and translational initiation. PRAK is a newly identified kinase shown to phosphorylate small heat shock proteins. Upon activation, MAPKAP-K2/3 can phosphorylate small heat shock protein (HSP27), lymphocyte-specific protein 1 (LSP1), cAMP response element binding protein (CREB), ATF1 and tyrosine hydroxylase. It was recently shown that p38 was actually associated with MAPKAP-K2, and phosphorylation of MAPKAP-K2 by p38 was required for this complex to be exported from the nucleus to the cytoplasm to phosphorylate the cytosolic targets such as HSP27.

Exposure to stress leads to changes not only in the nucleus and the cytoplasm, but also in the endoplasmic reticulum (ER). ER is an organelle specialized for protein folding and assembly of membrane proteins and of proteins destined for trafficking to lysosomes and for secretion. In the lumen of ER, many chaperone proteins facilitate the protein folding process. When cells are exposed to conditions that disrupt protein folding or there are unfolded or unassembled proteins in the ER, the transcription of many of the genes encoding ER resident proteins, such as the GRPs including Bip and GRP94, is upregulated. The unfolded protein response (UPR) in cells detects unfolded proteins in the ER lumen to activate transcription of selective genes in the nucleus. Recently, Ire1P was cloned and identified as an essential proximal sensor of this UPR pathway. On activation of UPR, Ire1P elicits an endonuclease activity that specifically cleaves an intron from the HAC1 mRNA, resulting in more efficient translation. The consequently increased level of the HAC1 protein leads to transcription activation of genes containing a UPRE (Unfolded Protein Response Element), including many genes encoding ER resident proteins.

ER is also the major intracellular reservoir of $Ca^{2+}$ in non-muscle cells. Many ER chaperones, including GRPs, calnexin and calreticulin, are $Ca^{2+}$ binding proteins and regulate $Ca^{2+}$ accumulation and release in ER, thereby controlling the intracellular $Ca^{2+}$ homeostasis. Sequestration of $Ca^{2+}$ by ER plays an important role in signal transduction and is essential for a number of vital cellular functions including translation, protein processing and cell division. ER is a primary target for oxidative damage, which decreases the amount of $Ca^{2+}$ sequestered within the ER by inhibiting the $Ca^{2+}$-ATPase uptake pump and by increasing the efflux of $Ca^{2+}$ through ER-associated channels. The resulting increase of $Ca^{2+}$ concentration in the cytoplasm has been proposed to exacerbate oxidative stress, damage mitochondria, activate $Ca^{2+}$-dependent degradation enzymes and disrupt the cytoskeleton.

Even though p38 and ER represent two important cellular stress response pathways, so far there have been no studies linking them together. The present invention relates to the cloning and identification of a novel protein, p46, which is rapidly phosphorylated when cells are exposed to various stresses. The phosphorylation was p38 dependent because specific inhibitors for p38 could completely abolish this effect. Using EGFP-p46 fusion proteins, p46 was found to be localized in endoplasmic reticulum. Downregulation of p46 using antisense oligonucleotides resulted in cytotoxicity and slowed cell growth, suggesting that p46 normally carries out functions on ER that are important for cell growth and viability. Significant downregulation of the major p46 transcript was observed in four out of four cases of brain tumors, suggesting that this process may be involved in tumor development and growth in brain.

The p46 gene encodes a protein of 373 amino acids. Searching the sequence against GenBank using BLAST program showed that while the amino-terminal (N-terminal) part of p46 (amino acids 1–187) had little homology to other genes, its carboxy-terminal (C-terminal) part shared significant homology to the C-terminal part of human neuroendocrine-specific proteins (NSPs). NSPs include NSP-A, NSP-B and NSP-C, which are encoded by different mRNAs transcribed from the same gene. Other NSP-like proteins have also been identified. While the functions of NSPs are unknown, studies have implicated their possible roles in cancer. At least NSP-C has been localized in the membrane of ER. Similarly, the p46 protein of the invention also carries a potential C-terminal ER retention signal (KRKAE), of which the motif consists of two lysine residues at the (−3) and either the (−4) or (−5) positions from the C-terminus.

Subsequent to the present discovery of this stress-related protein, there were reports in the literature of a protein referred to as Nogo, which exists in three forms. Nogo A is a protein of about 1,192 amino acids. Nogo B is a shorter form and is missing amino acids 186–1004. Nogo C is similar to Nogo B, but has a smaller amino terminal domain. (Prinjha, R. et al., Nature 403:383–384, 2000.) The inventors have determined that Nogo B corresponds to the protein of the present invention, so for consistency, the term Nogo B is used herein to refer to the novel protein of the invention.

Prinjha et al. reported that Nogo A, as a bivalent Fc fragment, is an inhibitor of neurite outgrowth. However, the functions and activity of Nogo B and Nogo C were not identified conclusively. (Goldberg, J. L. et al., Nature 403: 369–370, 2000).

According to the invention, when the Nogo B gene was expressed at an in-frame position at 3' of the EGFP gene, the fusion protein showed a localization pattern typical of ER distribution. Moreover, EGFP alone could be released by digitonin, yet the EGFP-Nogo B fusion protein, like Nogo B, could only be released by NP-40. Therefore, although Nogo B does not carry a signal peptide, it is very likely to be localized in ER.

Like neuroendocrine-specific proteins, Nogo B has two long hydrophobic regions at the C-terminal part: amino acids 198–235 and 289–335. They are composed of consecutive hydrophobic residues, making them less likely to be traditional transmembrane domains. Searching the protein sequence against PROSITE database using PFAMPROT program showed that the C-terminal part of the protein shared significant homology to the signature patterns of Flagella transport protein FLIP family (FIG. 5C), which are involved in the transport of flagellar proteins and also in a variety of signal peptide-independent secretion systems. The flagellar biosynthetic protein FLIP also carries very long hydrophobic regions, which are hypothesized to be embedded in the membrane and to act as an anchor for other proteins in the complex. Indeed, NSP-C has been localized in the ER membrane. The C-terminal part of Nogo B may also serve as an anchor in the ER membrane, because in size-fractionation experiments, the majority of Nogo B is present in a complex larger than 200 KD.

Nogo B is a protein abundant in normal human fibroblasts, since it represents about 1/2000 of the total protein solubilized by NP-40. Its presence on ER, therefore, suggests important functions. Antisense oligonucleotides complementary to the Nogo B mRNA were used to specifically downregulate Nogo B. As described in the Examples, all four antisense oligonucleotides efficiently and significantly decreased the levels of Nogo B. Treated cells underwent apoptosis, and the remaining cells showed abnormal morphology and slowed growth. Cytotoxicities conferred by different oligonucleotides were different. However, for each specific oligonucleotide, the level of downregulation of Nogo B correlated well with the apparent cytotoxicity. Less cytotoxicity was observed with antisense oligonucleotide AS2-1 than with AS2-2, while significantly more Nogo B remained with AS2-1 (FIGS. 9A and 9B). When cells were plated at a higher density for treatment with oligonucleotides, less cytotoxicity was observed and downregulation of Nogo B was also lower. These data indicate that at least part of the cytotoxic effect is a result of Nogo B downregulation, suggesting that Nogo B plays an important role in maintaining normal cell viability and proliferation.

Figure 3:
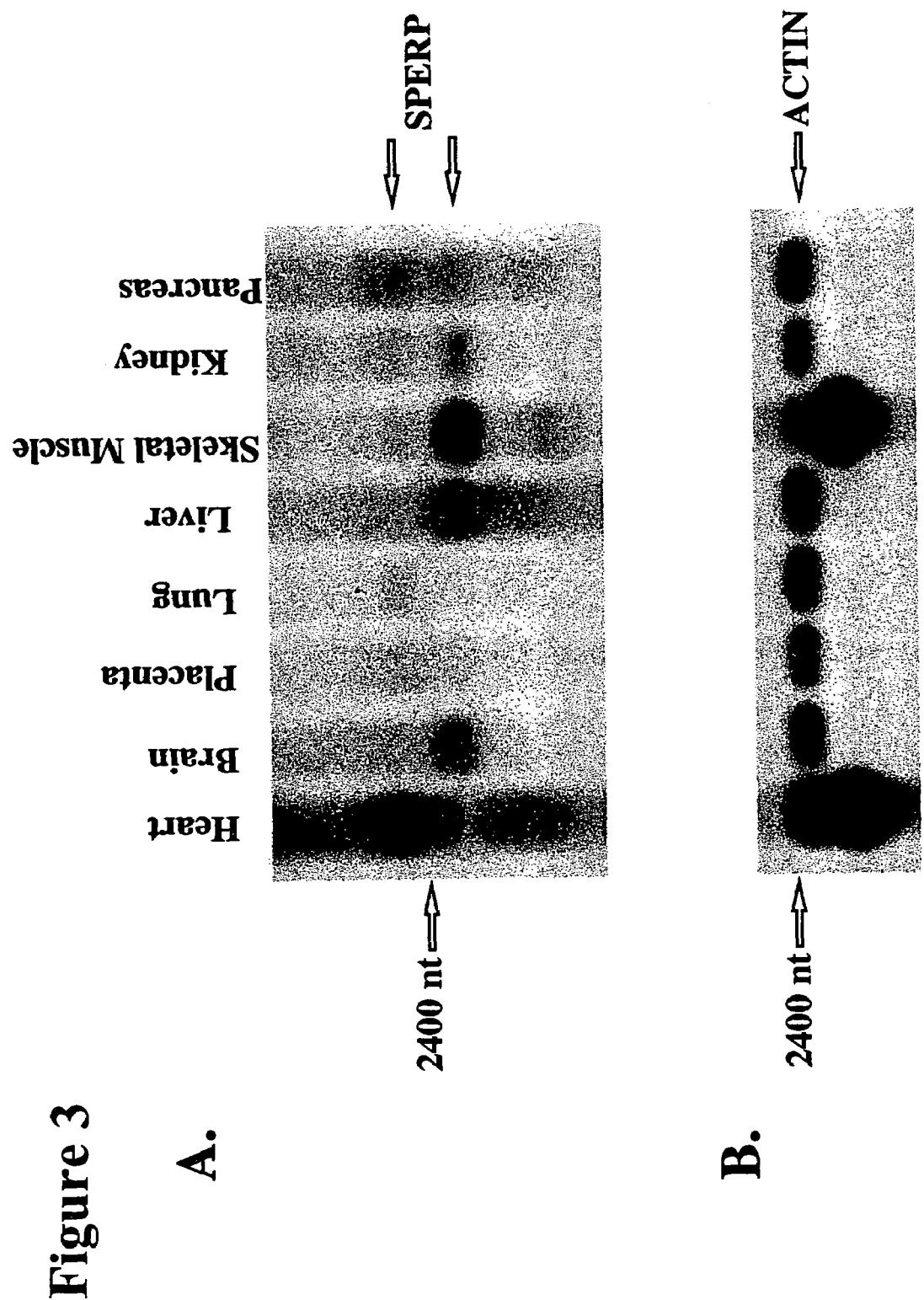
FIG. 3. Tissue-specific expression of the Nogo gene. (A). A Northern Blot containing mRNA from different tissues was probed with the full-length Nogo B cDNA. Positions of the two major Nogo transcripts were shown. The position of the 2.4 KB RNA marker was also indicated. (B). The same blot was stripped and reprobed with the cDNA for β-actin. Positions of the actin transcript and the 2.4 KB RNA marker were shown.

According to the invention, Nogo B normally exists in unphosphorylated and hypophosphorylated forms. When cells are exposed to various stresses, Nogo B rapidly becomes hyperphosphorylated in a dose-dependent manner. The hyperphosphorylation is likely to be a result of p38 activation because these stress conditions activate p38 and the presence of very low concentrations (close to IC50) of specific inhibitors against p38 completely abolished the hyperphosphorylation (FIGS. 1–3). Furthermore, the N-terminal part of Nogo B contains two putative phosphorylation sites for MAPKAP-K2 (FIG. 5A), which has been shown to be activated by p38. Even though the majority of Nogo B existed in a complex of about 200 kD in normal cells, the size of the complex was not significantly affected by hyperphosphorylation, suggesting that hyperphosphorylation was unlikely to result in dissociation of the complex or association of any additional factors. Rather, this hyperphosphorylation might lead to conformational changes and, consequently, alteration of the normal functions of the Nogo B complex, which may in turn help the ER cope with the stress condition.

ER has been shown to be involved in the stress response via two pathways: unfolded protein response initiated by detection of unfolded or misfolded proteins in ER, and the $Ca^{2+}$ response. In conditions where hyperphosphorylation of Nogo B was observed, such as UVC irradiation, no significant increase of GRP78 or GRP94, indicative of UPR, could be detected. Therefore it is unlikely that Nogo B plays a role in the UPR pathway. The $Ca^{2+}$ response, on the other hand, occurred rapidly, similar to that of Nogo B hyperphosphorylation. The abundance of Nogo B also makes it a likely candidate to modulate the $Ca^{2+}$ ATPase and/or $Ca^{2+}$ channels.

There were two major transcripts for Nogo B in human tissues: one at 2.6 KB and the other at 2.3 KB (FIG. 7A). Different transcripts may be a result of alternative splicing. The transcripts show strong tissue-specific distribution. While the 2.6 KB transcript showed highest levels of expression in the heart, the levels of the 2.3 KB transcript were the highest in skeletal muscle, liver and brain (FIG. 7A). In muscle cells, smooth ER is abundant and further develops into the sarcoplasmic reticulum, which specializes in controlling $Ca^{2+}$ uptake and release. Smooth ER is also abundant in cells active in lipid metabolism, such as hepatocytes. The observation of the relatively high level of Nogo B transcripts, and, very likely, the Nogo B protein in those tissues, is consistent with an important role for Nogo B in ER function. Taking into consideration that Nogo B is a downstream target of p38, it is of interest that these tissues are also constantly exposed to various stresses, which could trigger the activation of p38. For example, high aortic pressure or ischemial/reperfusion in perfused rat heart led to p38 activation. $H_2O_2$ can induce myocardial TNF production via a p38-dependent pathway. MAPKAP-K2, which is one of the kinases activated by p38, has been shown to have the highest expression in heart and skeletal muscle.

The major transcript in the brain, the 2.3 KB transcript, was almost completely lost in the four brain tumor samples studied, suggesting that Nogo B may be involved in tumorigenesis in brain. This observation is not inconsistent with an important role of Nogo B in cell growth and viability, since the 2.6 KB transcript remained in the tumor cells and may provide enough Nogo B for maintaining cell growth. Alternatively, the presence of the 2.3 KB transcript as the major transcript may be a result of factor(s) present only in well-differentiated normal brain cells. The factor(s) may be lost in brain tumor cells, which are usually less differentiated, leading to the loss of the 2.3 KB transcript. This is supported by the fact that the four tumor samples studied were of three distinct types, i.e., meningioma, glioma and malignant lymphoma. In either case, the 2.3 KB transcript may be used as a diagnostic or prognostic marker for brain tumors.

The loss of a Nogo B transcript in brain tumor samples may be consistent with the recent identification of the Nogo family as a potential inhibitor of nerve regeneration. Thus, replacement of the missing Nogo B polynucleotide and/or protein may help to regulate brain tumor cell growth.

It has also been suggested that myelin inhibitory activity of neuron regeneration is released after tissue injury. (Davies, S. J. et al., *J. Neurosci.* 19:5810–5822, 1999.) This is consistent with the present results, which show phosphorylation of Nogo B during activation of the stress response pathway in cells.

Nogo B appears to be the first ER protein shown to be phosphorylated as a result of p38 activation. This phosphorylation occurs rapidly. Evidence herein suggests that Nogo B plays an important role in cell growth and viability. Hyperphosphorylation of Nogo B may lead to conformational changes that result in alteration of its normal function in ER. The present invention provides the first evidence to link p38 to the ER functions when cells are exposed to stress.

Nucleic acid molecules of the invention include the sequence set forth in SEQ ID NO:1, sequences encoding the amino acid sequences set forth in SEQ ID NO:2, the sequence deposited as ATCC Accession No. PTA-89, and fragments, variants and derivatives thereof. Such variants will share at least 65% sequence identity, generally 68%, 70%, 80%, preferably 90%, 95%, 96%, 97%, 98%, or 99% sequence identity with the polynucleotide sequence of SEQ ID NO:1, polynucleotides encoding the amino acid sequence of SEQ ID NO:2 and the polynucleotide deposited as ATCC Accession No. PTA-89. Sequence identity can be determined using any algorithms known in the art, including but not limited to the following algorithm: Global DNA sequence identity is greater than 65% as determined by the Smith-Waterman homology search algorithm as implemented in MPSRCH program (Oxford Molecular) using an affine gap search with the following search parameters: gap open penalty: 12, gap extension penalty: 1.

As indicated above, the sequence of the invention is an endoplasmic reticulum protein. Analysis of the protein sequence of this novel protein using the Kyte-Doolittle program showed that there are two hydrophobic regions (aa 198–238 and aa 290–335), both of which are flanked by charged residues, suggesting that there are two transmembrane domains. Each domain may penetrate the membrane twice because a regular single-span transmembrane domain consists of about 20 amino acids. At the C terminus, there is an ER retention signal (KRYAE) (SEQ ID NO:11). The novel protein appears to be located in (or on) the endoplasmic reticulum (ER).

Polypeptides of the invention encompass the sequences set forth herein as well as derivatives, analogs and variants thereof. Variants include substantially homologous proteins having at least about 65%, typically at least about 70–75%, more typically at least about 80–85%, and most typically at least about 90–95%, 96%, 97%, 98%, or 99% homology. It is recognized that amino acid substitutions may be made, particularly conservative substitutions. See, Bowleetal (1990) *Science* 247:1306–1310. A variant polypeptide can differ in amino acid sequence by one or more substitutions, deletions, insertions, inversions, fusions and truncations or a combination of any of these. Variants can be naturally-occurring or can be made by recombinant means or chemical synthesis. Variant polypeptides may be fully functional or lack function in one or more activities.

Amino acids in the protein that are essential for function can be identified by site-directed mutagenesis, alanine-scanning mutagenesis (Cunningham et al. (1989) *Science* 244:1081–1085), etc. The resulting mutant molecules are then tested for biological activity. Critical sites for receptor binding can be determined. As described in, for example, Smith et al. (1992) *J. Mol. Biol.* 224:899–904; de Vos et al. (1992) *Science* 255:306–312.

The amino acid sequence of Nogo B polypeptide can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. Thus, the polypeptides of the present invention may include one or more amino acid substitutions, deletions or additions, either from natural mutations or human manipulation.

The invention therefore further includes variations of the Nogo B polypeptide which show substantial Nogo B polypeptide activity or which include regions of Nogo B protein such as the protein portions discussed below. Such mutants include deletions, insertions, inversions, repeats, and type substitutions. Guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Of particular interest are substitutions of charged amino acids with another charged amino acid and with neutral or negatively charged amino acids. The latter results in proteins with reduced positive charge to improve the characteristics of the Nogo B proteins. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331–340 (1967); Robbins et al., *Diabetes* 36:838–845 (1987); Cleland et al., *Crit. Rev. Therapeutic Drug Carrier Systems* 10:307–377 (1993)).

Amino acids in the polypeptides of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as the ability to become phosphorylated. It may be desirable to use this method to obtain a Nogo B variant that cannot be phosphorylated, and such variants are within the scope of the invention. Sites that are critical for ligand-receptor binding can also be determined by structural analysis such as crystallization, nuclear magnetic resonance or photoaffinity labeling (Smith et al., *J. Mol. Biol.* 224:899–904 (1992), and de Vos et al., *Science* 255:306–312 (1992)).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given Nogo B polypeptide will not be more than 50, 40, 30, 25, 20, 15, 10, 5 or 3.

Several regions are of particular importance in Nogo B. The C terminus of this novel protein (amino acids (aa) 188–373), is highly homologous to the C terminus of the human neuroendocrine-specific protein, which exists specifically in neurons and has been localized to the ER, and whose function is not clear. The N terminus of Nogo B shares little homology to any known proteins. The C terminus (aa 206 to aa 327) also shares homology to Flagella transport protein, FLIP, family signatures. Proteins evolutionarily related to FLIP have been found in a wide range of bacteria and are involved in a variety of signal-peptide independent secretion systems.

Another aspect of the invention is a chimeric polypeptide comprising a Nogo B polypeptide, or fragment thereof, and a polypeptide of interest. The invention therefore provides a chimeric polypeptide comprising a Nogo B polypeptide, or fragment thereof, fused to a polypeptide of interest, referred to as a second polypeptide. Nucleotide sequences encoding chimeric Nogo B and Nogo B polypeptides are also provided. In preferred embodiments the Nogo B polypeptide or fragment thereof is not normally found fused to the second polypeptide.

Yet another object of the invention is to provide polynucleotides that encode the mutants, fragments, and derivatives, as well as the native Nogo B. These polynucleotides can be operably linked to heterologous promoters to form expression cassettes. The expression cassettes can be introduced into suitable host cells for expression of Nogo B and/or Nogo B polypeptides and derivatives thereof.

Another object of the invention is to provide a transformed cell transiently expressing or having stably incorporated into its genome an expression vector comprising a promoter operably linked to a nucleotide sequence encoding a Nogo B or Nogo B polypeptide, or a fragment, derivative, mutant or fusion thereof.

The compositions of the invention comprise amino acid and nucleotide sequences for Nogo B. Such compositions have several uses including modulation of stress levels and cellular stress response, modulation of cell growth and viability, diagnosis and treatment of cancer and malignant growth, and diagnosis and treatment of other Nogo B related diseases.

"Fragments" possess the same amino acid sequence as the native or mutant Nogo B polypeptides except the fragments lack the amino, internal, and/or carboxyl terminal sequences of the native or mutant polypeptide.

"Derivatives" possess the same amino acid sequence as the native, mutant or fragment Nogo B but may contain amino acid substitutions, deletions, glycosylated residues, or other chemical modifications.

"Fusions" or "chimeric polypeptides" are mutants or fragments of the native Nogo B that also include amino and/or carboxyl terminal amino acid extensions.

The number or type of the amino acid substitutions is not critical, nor is the length or number of the amino acid deletions, or amino acid extensions that are incorporated in the Nogo B polypeptides. However, all of these polypeptides will exhibit, at least about 20% of one of the activities of the native Nogo B. More typically, the polypeptides exhibit at least about 40%, even more typically the polypeptides exhibit at least about 60% of one of the native Nogo B activities. All these polypeptides will retain at least about 50% amino acid identity with SEQ ID NO:2, more typically at least about 60%; even more typically, at least about 80%. Preferably, these polypeptides will retain at least about 85% amino acid sequence identity with SEQ ID NO:2; more preferably, at least about 90%; even more preferably, at least about 95%, 96%, 97%, 98%, or 99%.

"Nogo B activities" include modulation of the ER stress response, modulation of storage and exchange of calcium, regulation of oxidative stress, activation of ER downstream signaling, modulation of oxidant toxicity, modulation of cell growth and viability, ability to become hyperphosphorylated, modulation of oxidation and oxidative damage, modulation of calcium uptake, modulation of cellular stress response, inhibition of neurite outgrowth, neuron growth, and axon regeneration. A specific assay for activity is the hyperphosphorylation assay described in Example 2.

Expression of Nogo B and Nogo B Polypeptides

Preferably, Nogo B polypeptides are produced by recombinantly engineered host cells. These host cells are constructed by the introduction of an expression vector, preferably comprising a promoter operably linked to a Nogo B polypeptide coding sequence.

Such coding sequences can be constructed by synthesizing the entire gene or by altering existing Nogo B polypeptide coding sequences. Nogo B polypeptides can be divided into four general categories discussed above: mutants, fragments, fusions, and the native Nogo B polypeptides. The Nogo B polypeptides are those that occur in nature. The amino acid sequence of such polypeptides may vary slightly from SEQ ID NO:2. The native Nogo B and Nogo B polypeptide coding sequence can be selected based on the amino acid sequence shown in SEQ ID NO:2. For example, synthetic genes can be made using codons preferred by the host cell to encode the desired polypeptide. (See Urdea et al., (1983) *Proc. Natl. Acad. Sci. USA* 80:7461.) Alternatively, the desired native Nogo B polypeptide coding sequences can be cloned from nucleic acid libraries. Techniques for producing and probing nucleic acid sequence libraries are described, for example, in Sambrook et al. (1989) *Molecular Cloning: A Laboratory Manual* (New York, Cold Spring Harbor Laboratory). Other recombinant techniques, such as site specific mutagenesis, PCR, enzymatic digestion and ligation, can also be used to construct the desired Nogo B polypeptide coding sequence.

The native Nogo B polypeptide coding sequences can be modified to create the other classes of Nogo B polypeptides. For example, mutants can be created by making conservative amino acid substitutions that maintain or enhance native Nogo B or Nogo B activity. The following are examples of conservative substitutions: Gly⇔Ala; Val⇔Ile⇔Leu; Asp⇔Glu; Lys⇔Arg; Asn ⇔Gln; and Phe⇔Trp⇔Tyr. Mutants can also contain amino acid deletions or insertions compared to the native Nogo B polypeptides. Mutants may include substitutions, insertions, and deletions of the native polypeptides.

Fragments of the Nogo B protein are also within the scope of the invention. Preferred fragments comprise 10, 15, 20, 25, 30, 50, 75, 100, 125, 150, 175, 200, 225, 250, 275, 300, 325, 330, 340, 345, 350, 355, 360, 365, 368, 370 or 372 contiguous amino acids of SEQ ID NO:2. Particularly preferred fragment comprise either amino acids 1–368 or 2–368 of SEQ ID NO:2. Other preferred fragments comprise (a) contiguous amino acids about 1 to about 197 and about 236 to about 373 wherein amino acids about 197 and about 236 are joined by a peptide bond; (b) contiguous amino acids about 1 to about 288 and about 336 to about 373 wherein amino acids about 288 and about 336 are joined by a peptide bond; or (c) amino acids about 1 to about 197, about 236 to about 288, and about 336 to about 373, wherein amino acids about 197 and about 236 are joined by a peptide bond and amino acids about 288 and about 336 are joined by a peptide bond. Embodiments (a), (b) and (c) may be varied by the omission of some or all of amino acids 368–373.

Other preferred fragments include contiguous amino acids about 198 to about 235 or about 289 to about 335 of SEQ ID NO:2; contiguous amino acids about 1 to about 187 of SEQ ID NO:2; contiguous amino acids about 2 to about 187 of SEQ ID NO:2; and contiguous amino acids about 1 to about 198 of SEQ ID NO:2.

The fragments described above can be prepared by proteolysis of the corresponding protein or portion thereof, or by expression of a polynucleotide sequence encoding the amino acids of the fragment as described herein. Preferred polynucleotide fragments include 10, 15, 20, 25, 50, 75, 100, 125, 150, 175, 200, 250, 300, 350, 400, 450, 500, 550, 600, 650, 700, 750, 800, 850, 900, 925, 950, 975, 1000, 1025, 1050, 1075, 1090, 1110, 1115, 1110, 1115, 1116, 1125, 1150, 1175, 1200, 1250, 1300, 1350, 1400, 1450, 1500, 1550, 1600, 1650, 1700, 1750, 1800, 1850, 1900, 1950, 2000, 2050, 2100, 2125, 2150, 2175, 2200, 2210, 2220, or 2201 contiguous polynucleotides of SEQ ID NO:1.

Expression Vectors

An expression vector preferably will contain a promoter which is operable, that is, drives expression in the host cell and is operably linked to a Nogo B coding sequence. Sequences that modulate gene expression, such as enhancers and binding sites for inducers or repressors, may be present. Expression vectors may also include signal sequences, terminators, selectable markers, origins of replication, and sequences homologous to host cell sequences. These additional elements are optional but can be included to optimize expression, and are known in the art.

A Nogo B polypeptide coding sequence may also be linked in reading frame to a signal sequence. The signal sequence fragment typically encodes a peptide comprised of hydrophobic amino acids which directs the Nogo B polypeptide to the cell membrane or other subcellular compartment. Preferably, there are processing sites encoded between the leader fragment and the Nogo B polypeptide or fragment thereof that can be cleaved either in vivo or in vitro. DNA encoding suitable signal sequences can be derived from genes for secreted endogenous host cell proteins, such as the yeast invertase gene (EP. 12 873; JP 62,096,086), the A-factor gene (U.S. Pat. No. 4,588,684), and the interferon signal sequence (EP 60 057).

Typically, terminators are regulatory sequences, such as polyadenylation and transcription termination sequences, located 3' or downstream of the stop codon of the coding sequences. Usually, the terminator of native host cell proteins are operable when attached 3' of a Nogo B polypeptide coding sequence. Examples are the *Saccharomyces cerevisiae* alpha-factor terminator and the baculovirus terminator. Further, viral terminators are also operable in certain host cells; for instance, the SV40 terminator is functional in CHO cells.

Expression vectors may be integrated into the host cell genome or remain autonomous within the cell. Polynucleotide sequences homologous to sequences within the host cell genome may be needed to integrate the expression cassette. The homologous sequences do not always need to be linked to the expression vector to be effective. For example, expression vectors can integrate into the CHO genome via an unattached dihydrofolate reductase gene. In yeast, it is more advantageous if the homologous sequences flank the expression cassette. Particularly useful homologous yeast genome sequences are those disclosed in PCT WO 90/01800, and the HIS4 gene sequences, GenBank Accession No. J01331.

Purification

The purified Nogo B polypeptides are useful as compositions, for assays, and to produce antibodies.

Nogo B polypeptides can be isolated by a variety of steps including, for example, anion exchange chromatography, size exclusion chromatography, hydroxylapatite chromatography, hydrophobic interaction chromatography, metal chelation chromatography, reverse phase HPLC, affinity chromatography, and further ammonium sulfate precipitations. These techniques are well known to those of skill in the art.

For ligand binding studies, and other in vitro assays, the crude cell membrane fractions can be utilized. These membrane extracts can be isolated from cells that express Nogo B polypeptides, by lysing the cells. Alternatively, whole cells, expressing Nogo B polypeptides, can be cultured in a microliter plate.

Antibodies

Antibodies against Nogo B polypeptides are useful for affinity chromatography, immunofluorescent assays, and distinguishing Nogo B polypeptides.

Antibodies to the proteins of the present invention, both polyclonal and monoclonal, may be prepared by conventional methods known to those skilled in the art. For example, monoclonal antibodies are prepared using the method of Kohler et al. (1975) *Nature* 256:495–496, or a modification thereof.

If desired, the antibodies (whether polyclonal or monoclonal) may be labeled using conventional techniques. Suitable labels include fluorophores, chromophores, radioactive atoms (particularly $^{32}P$ and $^{25}I$), electron-dense reagents, enzymes, and ligands having specific binding partners. Enzymes are typically detected by their activity. For example, horseradish peroxidase is usually detected by its ability to convert 3,3',5,5'-tetra-methylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb.

Further, one may combine various labels for desired effect. For example, MAbs and avidin also require labels in the practice of this invention: thus, one might label a MAb with biotin, and detect its presence with avidin labeled with $^{125}$I, or with an anti-biotin MAb labeled with HRP. Other permutations and possibilities will be readily apparent to those of ordinary skill in the art, and are considered as equivalents within the scope of the instant invention.

Anti-Sense Molecules and Ribozymes

Inhibitors of the present invention include anti-sense molecules that, when administered to mammalian cells, are effective in reducing, for example, intracellular protein levels of Nogo proteins, specifically Nogo B. Anti-sense molecules bind in a sequence-specific manner to nucleic acids, such as mRNA or DNA. When bound to mRNA that has complementary sequences, anti-sense molecules prevent translation of the mRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. *Nucl. Acids Res.* 21:3405–3411 (1993), which describes dumbbell anti-sense oligonucleotides).

Anti-sense technology can be used to control gene expression through triple-helix formation, which promotes the ability of the double helix to open sufficiently for the binding of polymerases, transcription factors or regulatory molecules. See Gee et al., In Huber and Carr, "Molecular and Immunologic Approaches," Futura Publishing Co. (Mt. Kisco, N.Y.; 1994). Alternatively, an anti-sense molecule may be designed to hybridize with a control region of the Nogo B gene, e.g., promoter, enhancer or transcription initiation site, and block transcription of the gene; or block translation by inhibiting binding of a transcript to ribosomes. See generally, Hirashima et al. in *Molecular Biology of RNA: New Perspectives* (M. Inouye and B. S. Dudock, eds., 1987 Academic Press, San Diego, p. 401); *Oligonucleotides: Anti-sense Inhibitors of Gene Expression* (J. S. Cohen, ed., 1989 MacMillan Press, London); Stein and Cheng, *Science* 261:1004–1012 (1993); WO 95/10607; U.S. Pat. No. 5,359,051; WO 92/06693; and EP-A2-612844 each of which is incorporated herein by reference.

Briefly, such molecules are constructed such that they are complementary to, and able to form Watson-Crick base pairs with, a region of transcribed Nogo B mRNA sequence. The resultant double-stranded nucleic acid interferes with subsequent processing of the mRNA, thereby preventing protein synthesis.

In general, a portion of a sequence complementary to the Nogo B coding region may be used to modulate gene expression. Alternatively, cDNA constructs that can be transcribed into anti-sense RNA may be introduced into cells or tissues to facilitate the production of anti-sense RNA. Thus, as used herein, the phrase "anti-sense molecules" broadly encompasses anti-sense oligonucleotides whether synthesized as DNA or RNA molecules as well as all plasmid constructs that, when introduced into a mammalian cell, promote the production of anti-sense RNA molecules. An anti-sense molecule may be used, as described herein, to inhibit expression of Nogo B genes.

Anti-sense molecules for use as described herein can be synthesized by any method known to those of skill in this art including chemical synthesis by, for example, solid phase phosphoramidite chemical synthesis. See, e.g., WO 93/01286; U.S. Pat. No. 6,043,090; U.S. Pat. No. 5,218,088; U.S. Pat. No. 5,175,269; and U.S. Pat. No. 5,109,124, each of which is incorporated herein by reference. Alternatively, RNA molecules may be generated by in vitro or in vivo transcription of DNA sequences encoding the Nogo B cDNA, or a portion thereof, provided that the DNA is incorporated into a vector downstream of a suitable RNA polymerase promoter (such as, e.g., T3, T7 or SP6). Large amounts of anti-sense RNA may be produced by incubating labeled nucleotides with a linearized Nogo B cDNA fragment downstream of such a promoter in the presence of the appropriate RNA polymerase. Such anti-sense molecules are preferably at least 10, 15 or 20 nucleotides in length. More preferably, anti-sense molecules are at least 25 nucleotides in length. Within certain embodiments, an anti-sense molecule of the present invention will comprise a sequence that is unique to the Nogo B cDNA sequence or that can hybridize to the cDNA of Nogo B under conditions of high stringency. Within the context of the present invention, high stringency means standard hybridization conditions such as, e.g., 5× SSPE, 0.5% SDS at 65° C. or the equivalent thereof.

Anti-sense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrehedron Lett.* 28:3539–3542 (1987); Miller et al., *J. Am. Chem. Soc.* 93:6657–6665 (1971); Stec et al., *Tetrehedron Lett.* 26:2191–2194 (1985); Moody et al., *Nucl. Acids Res.* 12:4769–4782 (1989); Uznanski et al., *Nucl. Acids Res.* 17(12):4863–4871 (1989); Letsinger et al., *Tetrahedron* 40:137–143 (1984); Eckstein, *Annu. Rev. Biochem.* 54:367–402 (1985); Eckstein, *Trends Biol. Sci.* 14:97–100 (1989); Stein, in: *Oligodeoxynucleotides. Antisense Inhibitors of Gene Expression*, Cohen, Ed, Macmillan Press, London, pp. 97–117 (1989); Jager et al., *Biochemistry* 27:7237–7246 (1988)). Possible additional or alternative modifications include, but are not limited to, the addition of flanking sequences at the 5' and/or 3' ends and/or the inclusion of nontraditional bases such as inosine, queosine and wybutosine, as well as acetyl-methyl-, thio- and other modified forms of adenine, cytidine, guanine, thymine and uridine.

Within alternate embodiments of the present invention, Nogo B inhibitors may be ribozymes. A ribozyme is an RNA molecule that specifically cleaves RNA substrates, such as mRNA, resulting in specific inhibition or interference with cellular gene expression. As used herein, the term "ribozymes" includes RNA molecules that contain anti-sense sequences for specific recognition, and an RNA-cleaving enzymatic activity. The catalytic strand cleaves a specific site in a target RNA at greater than stoichiometric concentration.

A wide variety of ribozymes may be utilized within the context of the present invention, including for example, the hammerhead ribozyme (for example, as described by Forster and Symons, *Cell* 48:211–220 (1987); Haseloff and Gerlach, *Nature* 328:596–600 (1988); Walbot and Bruening, *Nature* 334:196 (1988); Haseloff and Gerlach, *Nature* 334:585 (1988)); the hairpin ribozyme (for example, as described by Haseloff et al., U.S. Pat. No. 5,254,678, issued Oct. 19, 1993 and Hempel et al., European Patent Publication No. 0 360 257, published Mar. 26, 1990); and Tetrahymena ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates), or chimerics thereof (e.g., DNA/RNA/RNA).

Ribozymes can be targeted to any RNA transcript and can catalytically cleave such transcripts (see, e.g., U.S. Pat. No. 5,272,262; U.S. Pat. No. 5,144,019; and U.S. Pat. Nos.

5,168,053, 5,180,818, 5,116,742 and 5,093,246 to Cech et al.). According to certain embodiments of the invention, any such Nogo B mRNA-specific ribozyme, or a nucleic acid encoding such a ribozyme, may be delivered to a host cell to effect inhibition of Nogo B gene expression. Ribozymes and the like may therefore be delivered to the host cells by DNA encoding the ribozyme linked to a eukaryotic promoter, such as a eukaryotic viral promoter, such that upon introduction into the nucleus, the ribozyme will be directly transcribed.

Proteins and Polypeptides

In addition to the anti-sense molecules and ribozymes disclosed herein, Nogo B inhibitors of the present invention also include proteins or polypeptides that are effective in either reducing Nogo B gene expression or in decreasing one or more of Nogo B's biological activities. A variety of methods are readily available in the art by which the skilled artisan may, through routine experimentation, rapidly identify such Nogo B inhibitors. The present invention is not limited by the following exemplary methodologies.

As discussed above, Nogo B is associated with apoptosis. Thus, inhibitors of Nogo B's biological activities encompass those proteins and/or polypeptides that interfere with Nogo B's role in cell growth and viability. Such interference may occur through direct interaction with Nogo B's ability to be phosphorylated or indirectly through non- or un-competitive inhibition such as via binding to an allosteric site. Accordingly, available methods for identifying proteins and/or polypeptides that bind to Nogo B may be employed to identify lead compounds that may, through the methodology disclosed herein, be characterized for their Nogo B inhibitory activity.

A vast body of literature is available to the skilled artisan that describes methods for detecting and analyzing protein—protein interactions. Reviewed in Phizicky, E. M. et al., *Microbiological Reviews* 59:94–123 (1995) incorporated herein by reference. Such methods include, but are not limited to physical methods such as, e.g., protein affinity chromatography, affinity blotting, immunoprecipitation and cross-linking as well as library-based methods such as, e.g., protein probing, phage display and two-hybrid screening. Other methods that may be employed to identify protein—protein interactions include genetic methods such as use of extragenic suppressors, synthetic lethal effects and unlinked noncomplementation. Exemplary methods are described in further detail below.

Inventive Nogo B inhibitors may be identified through biological screening assays that rely on the direct interaction between the Nogo B protein and a panel or library of potential inhibitor proteins. Biological screening methodologies, including the various "n-hybrid technologies," are described in, for example, Vidal, M. et al., *Nucl. Acids Res.* 27(4):919–929 (1999); Frederickson, R. M., *Curr. Opin. Biotechnol.* 9(J):90–6 (1998); Brachmann, R. K. et al., *Curr. Opin. Biotechnol.* 8(5):561–568 (1997); and White, M. A., *Proc. Natl. Acad. Sci. U.S.A.* 93:10001–10003 (1996) each of which is incorporated herein by reference. For example, inhibition of Nogo B can be detected by measuring neurite outgrowth in treated cells, as described by Prinjha et al, *Nature* 403:383–384 (2000), or by using other methods known in the art. Inhibition can also be detected by measuring axon regeneration in treated cells, as described by Grand Pre et al, *Nature* 403:439–444 (2000).

The two-hybrid screening methodology may be employed to search new or existing target cDNA libraries for Nogo B binding proteins that have inhibitory properties. The two-hybrid system is a genetic method that detects protein—protein interactions by virtue of increases in transcription of reporter genes. The system relies on the fact that site-specific transcriptional activators have a DNA-binding domain and a transcriptional activation domain. The DNA-binding domain targets the activation domain to the specific genes to be expressed. Because of the modular nature of transcriptional activators, the DNA-binding domain may be severed covalently from the transcriptional activation domain without loss of activity of either domain. Furthermore, these two domains may be brought into juxtaposition by protein—protein contacts between two proteins unrelated to the transcriptional machinery. Thus, two hybrids are constructed to create a functional system. The first hybrid, i.e., the bait, consists of a transcriptional activator DNA-binding domain fused to a protein of interest. The second hybrid, the target, is created by the fusion of a transcriptional activation domain with a library of proteins or polypeptides. Interaction between the bait protein and a member of the target library results in the juxtaposition of the DNA-binding domain and the transcriptional activation domain and the consequent up-regulation of reporter gene expression.

A variety of two-hybrid based systems are available to the skilled artisan that most commonly employ either the yeast Gal4 or *E. coli* LexA DNA-binding domain (BD) and the yeast Gal4 or herpes simplex virus VP16 transcriptional activation domain. Chien, C. -T. et al., *Proc. Natl. Acad. Sci. U.S.A.* 88:9578–9582 (1991); Dalton, S. et al., *Cell* 68:597–612 (1992); Durfee, T. K. et al., *Genes Dev.* 7:555–569 (1993); Vojtek, A. B. et al., *Cell* 74:205–214 (1993); and Zervos, A. S. et al., *Cell* 72:223–232 (1993). Commonly used reporter genes include the *E. coli* lacZ gene as well as selectable yeast genes such as HIS3 and LEU2. Fields, S. et al., *Nature (London)* 340:245–246 (1989); Durfee, T. K., supra; and Zervos, A. S., supra. A wide variety of activation domain libraries are readily available in the art such that the screening for interacting proteins may be performed through routine experimentation.

Screening for Agonists and Antagonists

Nogo B polypeptides can also be used to screen combinatorial libraries to identify agonist or antagonists. For example, a "library" of peptides may be synthesized following the methods disclosed in U.S. Pat. No. 5,010,175, and in PCT WO 91/17823, both incorporated herein by reference in full. The peptide library is first screened for binding to the selected Nogo B polypeptide. The peptides are then tested for their ability to inhibit or enhance Nogo B activity. Peptides exhibiting the desired activity are then isolated and sequenced.

Nogo B agonists or antagonists may be screened using any available method. The assay conditions ideally should resemble the conditions under which the Nogo B activity is exhibited in vivo, i.e., under physiologic pH, temperature, ionic strength, etc. Suitable agonists or antagonists will exhibit strong inhibition or enhancement of the Nogo B activity at concentrations that do not raise toxic side effects in the subject. Agonists or antagonists that compete for binding to the Nogo B polypeptide may require concentrations equal to or greater than the native Nogo B concentration, while inhibitors capable of binding irreversibly to the polypeptide may be added in concentrations on the order of the native Nogo B concentration.

Pharmaceutical Compositions

Pharmaceutical compositions can comprise polypeptides, antibodies, or polynucleotides of the claimed invention. The polynucleotides can include antisense oligonucleotides or ribozymes capable of specifically binding to Nogo B polynucleotides, as discussed above. The pharmaceutical compositions will comprise a therapeutically effective amount of polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician.

For purposes of the present invention, an effective dose will be from about 0.01 mg/kg to 50 mg/kg or 0.05 mg/kg to about 10 mg/kg of the polypeptide or DNA construct in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., New Jersey 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be mammals or birds. In particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a tumor or lesion. Other modes of administration include oral and pulmonary administration, suppositories, and transdermal applications, needles, and gene guns or hyposprays. Dosage treatment may be a single dose schedule or a multiple dose schedule.

Alternatively, the Nogo B polypeptides could be stably expressed in an organ of a mammal, and then the organ could be xenografted into a human in need of such treatment.

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adenoassociated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, Jolly et al. (1994) *Cancer Gene Therapy* 1:51–64; Kimura et al. (1994) *Human Gene Therapy* 5:845–852; Connelly et al. (1995) *Human Gene Therapy* 6:185–193; and Kaplitt et al. (1994) *Nature Genetics* 6:148–153.

Human adenoviral gene therapy vectors are also known in the art and employable in this invention. See, for example, Berkner et al. (1988) *Biotechniques* 6:616; Rosenfeld et al. (1991) *Science* 252:431; and WO 93/07283, WO 93/06223, and WO 93/07282. Exemplary known adenoviral gene therapy vectors employable in this invention include those described in the above referenced documents and in WO 94/12649, WO 93/03769, WO 93/19191, WO 94/28938, WO 95/11984, WO 95/00655, WO 95/27071, WO 95/29993, WO 95/34671, WO 96/05320, WO 94/08026, WO 94/11506, WO 93/06223, WO 94/24299, WO 95/14102, WO 95/24297, WO 95/02697, WO 94/28152, WO 94/24299, WO 95/09241, WO 95/25807, WO 95/05835, WO 94/18922, WO 95/09654. Alternatively, administration of DNA linked to killed adenovirus as described in Curiel et al. (1992) *Hum. Gene Ther.* 3:147–154 may be employed.

The gene delivery vehicles of the invention also include adenovirus associated virus (AAV) vectors. Leading and preferred examples of such vectors for use in this invention are the AAV-2 based vectors disclosed in Srivastava, WO 93/09239. Most preferred AAV vectors comprise the two AAV inverted terminal repeats in which the native D-sequences are modified by substitution of nucleotides, such that at least about 5 native nucleotides and up to 18 native nucleotides, preferably at least about 10 native nucleotides up to 15 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e., there is one sequence at each end) which are not involved in HP formation. The non-native replacement nucleotide may be any nucleotide other than the nucleotide found in the native D-sequence in the same position. Other employable exemplary AAV vectors are pWP-1 9, pWN1, both of which are disclosed in Nahreini et al. (1993) *Gene* 124:257–262. Another example of such an AAV vector is psub2O1. See Samulski et al. (1987) *J. Virol.* 61:3096. Another exemplary AAV vector is the Double-D ITR vector. Construction of the Double D ITR vector is disclosed in U.S. Pat. No. 5,478,745. Still other vectors are those disclosed in Carter, U.S. Pat. No. 4,797,368 and Muzyczka, U.S. Pat. No. 5,139,941, Chartejee, U.S. Pat. No. 5,474,935, and Kotin, PCT Patent Publication WO 94/288157. Yet a further example of an AAV vector employable in this invention is SSV9AFABTKneo, which contains the AFP enhancer and albumin promoter and directs expression predominantly in the liver. Its structure and construction are disclosed in Su, (1996) *Human Gene Therapy* 7:463–470. Additional AAV gene therapy vectors are described in U.S. Pat. No. 5,354,678, U.S. Pat. No. 5,173,414, U.S. Pat. No. 5,139,941, and U.S. Pat. No. 5,252,479.

EXAMPLE 1

General Methods

Antibodies and other reagents. Antibodies against human Cdc2 (SC-54) and GRP94 (SC-1794) were purchased from Santa Cruz Biotechnology (Santa Cruz, Calif.). $H_2O_2$, suramine, specific p38 inhibitors SB202190 and PD169316 were purchased from Calbiochem (San Diego, Calif.). The plasmid pLIB-EGFP and the antibody against GFP were purchased from Clontech (Palo Alto, Calif.). (±)-r-7,t-8-dihydroxy-t-9,10-epoxy-7,8,9,10-tetrahydrobenzo(a)pyrene (BPDE) was purchased from ChemSyn Laboratories (Lenexa, Kans.).

Cell culture and treatment. Normal human fibroblast IMR90 was purchased from American Type Culture Collection (Manassas, Va.). Cells were routinely cultured in Dulbecco's Modified Eagle's Medium (DMEM) containing 10% fetal bovine serum, 2 mM L-glutamine, 4.5 g/liter glucose, 100 units penicillin and 100 µg streptomycin at 37° C. under an atmosphere of 5% $CO_2$. For UV irradiation, cells were washed twice with phosphate-buffered saline (PBS) and then irradiated with appropriate doses of UVC (254 nm). Fresh complete medium was added back and cells were lysed at appropriate times. For treatment with BPDE, cells were washed with PBS twice and fresh DMEM was added. BPDE was dissolved in anhydrous dimethyl sulfoxide (DMSO) and appropriate amount of BPDE solution was added to DMEM. Cells were lysed 30 minutes later.

Preparation of cell lysates. Cells were trypsinized, counted and centrifuged at 1000 g for 3 min. Cell pellets were washed with PBS three times. For whole cell lysates, cells were resuspended in appropriate volume of the lysis buffer (150 mM Tris.HCl (pH 7.5), 150 mM NaCl, 0.5% NP-40, 50 mM NaF, 1 mM $Na_3VO_4$ and 1 mM DTT) containing the Complete Protease Inhibitor Cocktail (Boehringer Mannheim Corp, Indianapolis, Ind.), so that the final concentration was $1 \times 10^6$ cells/0.1 ml. After incubation on ice for 30 minutes, the lysate was centrifuged at 14000 g for 30 min, and the clear supernatant was frozen at −80° C. as the whole cell lysate. For fractionated cell extracts, cells were resuspended in appropriate volume of digitonin lysis buffer (5 mM $Na_2HPO_4$ (pH 7.4), 50 mM NaCl, 150 mM sucrose, 5 mM KCl, 1 mM $MgCl_2$, 0.5 mM $CaCl_2$, 1 mM $Na_3VO_4$, 1 mM DTT and 0.1% digitonin) with protease inhibitors for 5 minutes. The cell suspension was then centrifuged on a sucrose cushion (30% sucrose, 2.5 mM Tris.HCL (pH 8) and 10 mM NaCl) at 1000 g for 10 minutes. The supernatant was saved as Cytosol fraction. The pellet was resuspended in appropriate volume of nuclear lysis buffer (120 mM NaCl, 10 mM $Na_2HPO_4$ (pH 7.5), 0.5% NP-40, 1 mM $Na_3VO_4$ and 1 mM DTT). After 30 minutes, the mixture was centrifuged at 14000 g for 30 minutes, and the supernatant was saved as nuclear fraction.

Western Blotting. Lysates prepared from equal number of cells were mixed with equal volume of 2× sample buffer (50 mM Tris.HCl, pH 6.9, 9% glycerol, 2.3% SDS, 0.1% bromophenol blue and 10% mecaptoethanol) and the proteins were separated on a SDS/polyacrylamide gel. The proteins were then electroblotted onto an Immobilon-P membrane (Millipore, Bedford, Mass.). The blots were blocked for 1 hour at room temperature in Tris-buffered saline (20 mM Tris-HCl, pH 7.6, 137 mM NaCl) containing 0.1% (v/v) Tween 20 and 5% (w/v) non-fat dry milk (blocking solution), and then incubated for 1 hour at room temperature with appropriate antibodies at a concentration of 0.2–1 µg/ml. The blots were washed several times and then incubated with horseradish peroxidase-conjugated goat-anti-mouse IgG (Santa Cruz Biotechnology) that had been diluted 1:3000 with blocking solution. Enhanced chemiluminescence (Amersham, Arlington Heights, Ill.) was used according to the manufacturer's recommendations to detect the signal.

Protein purification and analysis. Nuclear fraction (200 mg) prepared from IMR90 was dialyzed into S buffer (10 mM Hepes [pH 7.2], 0.25 M sucrose, 2 mM DTT), loaded on an SP Sepharose column (Pharmacia, 1.6×10 cm), and eluted with a 120 ml gradient of 0–1 M sodium chloride. To assay for Nogo B, column fractions were analyzed by Western Blot using the anti-Cdc2 antibody. Column fractions enriched for Nogo B were pooled, dialyzed into Q buffer (10 mM Hepes [pH 8.6], 0.25 M sucrose, 2 mM DTT), and loaded on a Mono-Q column (Pharmacia, 0.5×5 cm). The column was eluted with a 45 ml 0–0.6M sodium chloride gradient. Column fractions were analyzed by Western blot and by SDS-PAGE stained with Commassie Brilliant Blue R. Peak fractions were concentrated by ultrafiltration and subjected to preparative SDS-PAGE purification.

Protein identification by mass spectrometry. The protein band observed by SDS-PAGE was excised and the protein was digested in-gel with trypsin according to the procedure of Shevchenko, A., et al., (1996) *Proc. Natl. Acad. Sci. USA*, 93:14440–14445. The peptides were extracted and desalted, and the peptide mixture was analyzed by nanoelectrospray tandem mass spectrometry (nanoES MS/MS) (Wilm, M., et al., (1996) *Nature (London)*, 379:466–469) using a PE-Sciex API III triple-quadrupole mass spectrometer. To identify the protein, the peptide sequence tags obtained by nanoES MS/MS were used to search an in-house non-redundant protein database using PeptideSearch software (Mann, M. (1994) in Microcharacterization of Proteins (Kellner, R., Lottspeich, F. and Meyer, H. E., Eds.) pp. 223–245.)

Internal Edman degradation sequencing. SDS-PAGE-purified protein was also transferred onto a PVDF membrane and analyzed by Internal Edman Degradation Sequencing (Fernandez, J., et al., (1994) *Anal. Biochem.* 218:112–118). Briefly, Nogo B was digested with trypsin, the eluted peptides were resolved by RP-HPLC, and selected peaks were subjected to N-terminal sequencing by Edman degradation. Peptide sequences were reverse translated and used to search the GenBank database using MPSRCH program to find matched sequences.

Retrovirus infection. The stop codon of the EGFP gene on pLIB-EGFP (Clontech) was mutated into an HindIII site using QuickChange Site-directed Mutagenesis kit (Stratagene). The NcoI-SspI fragment of the Nogo B gene was then ligated into this HindIII site. A 293-derived packaging cell line was transfected with PLIB-EGFP or pLIB-EGFP-Nogo B in combination with pMLR (encoding VSVG) using Calcium Phosphate Transfection Kit (Clontech) following the manufacturer's suggestions. Sixteen hours later, fresh medium with 1 mM NaB was added and cells were incubated at 32° C. for 2 days. The medium containing virus was filtered and added to exponentially growing IMR90 cells or GM00637 cells along with polybrene (8 mg/ml). The cells were centrifuged at 600 g for 1 hour and incubated at 32° C. overnight. Fresh complete medium was then added and cells were incubated at 37° C. for 2 days before being replated at lower density. Pictures of fluorescence images were taken under a microscope with a blue filter (485 nm).

Northern Blotting. Nylon membranes with RNA were incubated with appropriate volume of ExpressHyb solution (Clontech) for 1 hour at 68° C. The plasmid containing the full length Nogo B gene was labeled with $\alpha$-$^{32}$P-dCTP using Prime-It RmT Random Primer Labeling Kit (Stratagene), and added to the ExpressHyb solution. After 1 hour, the membrane was washed with ample volume of solution 1 (2×SSC and 0.0% SDS) at room temperature several times. The membrane was then washed with solution 2 (0.1×SSC and 0.1% SDS) at 50° C. for 40 minutes before being exposed to Hyperfilm MP (Amersham).

Treatment with antisense oligonucleotide. Antisense oligonucleotides were obtained from Sequitur Inc (Natick, Mass.). The four antisense oligonucleotides were: AS-1, CUGGAUAGCUUGGAUCACACCCUUG (SEQ ID NO:3); AS-2, CAACUUCAGGA-UUCCAGAUAUGCCC (SEQ ID NO:4); AS-3, AUUCCACCAGUGCCUCA-GAUAGGA (SEQ ID NO:5); and AS-4, AUGAUCUAU-CUGUGCCUGAUGCCG (SEQ ID NO:6). For treatment with antisense oligonucleotide, exponentially growing IMR90 cells were plated at 3×10$^5$ cells per 60 mm dish. After 24 hours, 4 µl of a particular oligonucleotide (100 µM) was mixed with 12 µl of Lipitoid I (0.5 mM) in Opti-MEM (Gibco-BRL) and added to the cell culture medium. After 16 hours, fresh complete medium was added. After another 24 hours, pictures were taken for the cells before cells were trypsinized, counted and lysed.

EXAMPLE 2

Identification of a Protein Hyperphosphorylated During Stress

During a study of the effect of ultraviolet irradiation on cell cycle regulation, two closely-migrated proteins with apparent molecular weight around 46 KD were identified (FIG. 7A). Upon irradiation with 20 J/m$^2$ of UVC, this doublet shifted very rapidly to a slower mobility form on a SDS polyacrylamide gel (FIG. 7A). At 2 hours after UV irradiation, about half of the protein changed back to the fast mobility form (FIG. 7B), as did most of the protein 20 hours later.

Since phosphorylation of a protein can lead to mobility shift on SDS-PAGE, the mobility shift of p46 was investigated to determine if it was due to phosphorylation. Protein lysates were prepared from irradiated cells in the absence of sodium orthovanadate. Incubation with alkaline phosphatase led to disappearance of the slow mobility form (FIG. 7C), indicating that the slow mobility form represented the hyperphosphorylated p46. Only the fastest migrating band remained when more phosphatase was added, indicating that it represented the unphosphorylated form of p46 (FIG. 7C).

Figure 7:
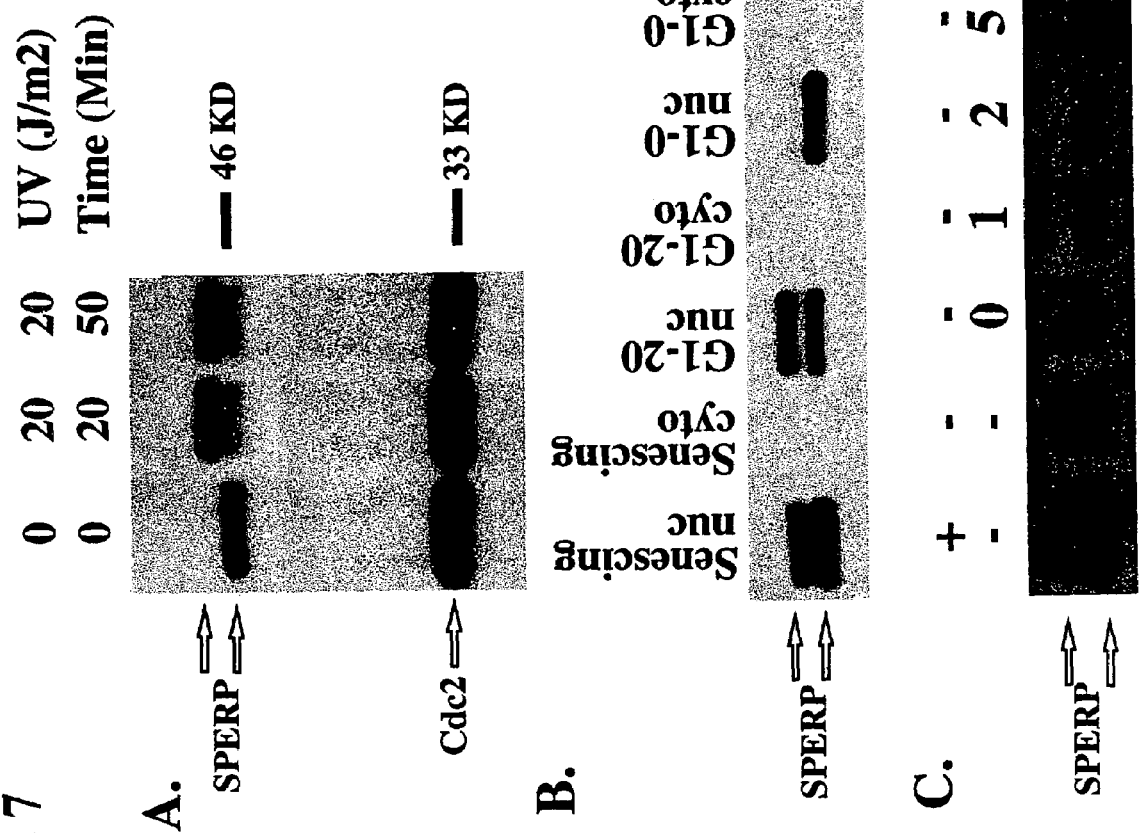
FIG. 7.

As shown in FIG. 7, Nogo B was hyperphosphorylated after UVC irradiation. (A) IMR90 cells were irradiated with 0 or 20 J/m$^2$ of UVC (254 nm) and were lysed 0, 20 or 50 minutes after irradiation. Lysates were separated on SDS-PAGE gels and transferred to a PVDF membrane, followed by being probed with a monoclonal antibody against human Cdc2 (SC-54). Positions of Cdc2 and Nogo B were shown by arrows. Sizes of molecular weight markers were indicated. (B) IMR90 cells were synchronized at G1 phase, irradiated with 0 (G1-0) or 20 J/m$^2$ (G1-20) of UVC and trypsinized 2 hours later. Senescing cells (Senescing) were IMR90 cells that were grown continuously until no obvious mitotic figure could be seen under microscope. Cells were trypsinized and lysed with digitonin followed by NP-40 as described in Example 1. Digitonin-solubilized fraction (Cyto) and NP-40-solubilized fraction (Nuc) were separated on SDS-PAGE. SC-54 was used for Western Blotting. (C) IMR90 cells were irradiated with 20 J/m$^2$ of UVC and lysed using buffers with or without vanadate two hours later. Lysates without vanadate were dialyzed against 0.1 M (NH4)$_2$SO$_4$ (pH 8.0) overnight, and incubated with 0, 1, 2, or 5 units of calf intestine alkaline phosphatase (CIAP) for 1 hour at 37° C. Lysates were separated on SDS-PAGE. SC-54 was used for Western Blotting.

UV irradiation has been shown to result in the formation of DNA photoproducts, increased level of free radicals, and changes in the plasma membrane such as aggregation of growth factor receptors. To test whether other DNA damaging agents could also lead to hyperphosphorylation of p46, cells were treated with various doses of benzo(a)pyrene diol epoxide, the major active metabolite of benzo(a)pyrene, which modifies the C-8 position of guanine. As shown in FIG. 4A, BPDE treatment led to p46 hyperphosphorylation in a dose-dependent manner. The role of the nucleotide excision repair system, which recognizes and repairs DNA adducts induced by UV and BPDE, was excluded because a similar extent of hyperphosphorylation was also observed in XP12BE cells derived from a patient belonging to complementation group A of xeroderma pigmentosa, in which nucleotide excision repair is defective. Changes in the plasma membrane were also unlikely to cause the p46 hyperphosphorylation, because a chemical agent such as BPDE is unlikely to change the plasma membrane structure in the same way as that hypothesized for UV, and preincubation of cells with suramin completely blocked the phosphorylation of ERK2, which is a major downstream effect of the UV-induced growth factor receptor aggregation, but had no effect on the p46 hyperphosphorylation (FIG. 4B).

Since p46 was also hyperphosphorylated in senescing human fibroblasts (FIG. 7B) and in cells arrested by aphidicolin, stress alone was investigated to determine if it was sufficient to induce the p46 hyperphosphorylation. As shown in FIG. 4C, treatment of cells with NaCl, H$_2$O$_2$ or sorbitol resulted in rapid hyperphosphorylation of p46. Therefore, it is concluded that the p46 hyperphosphorylation is due to elevated stress level in cells.

Figure 4:
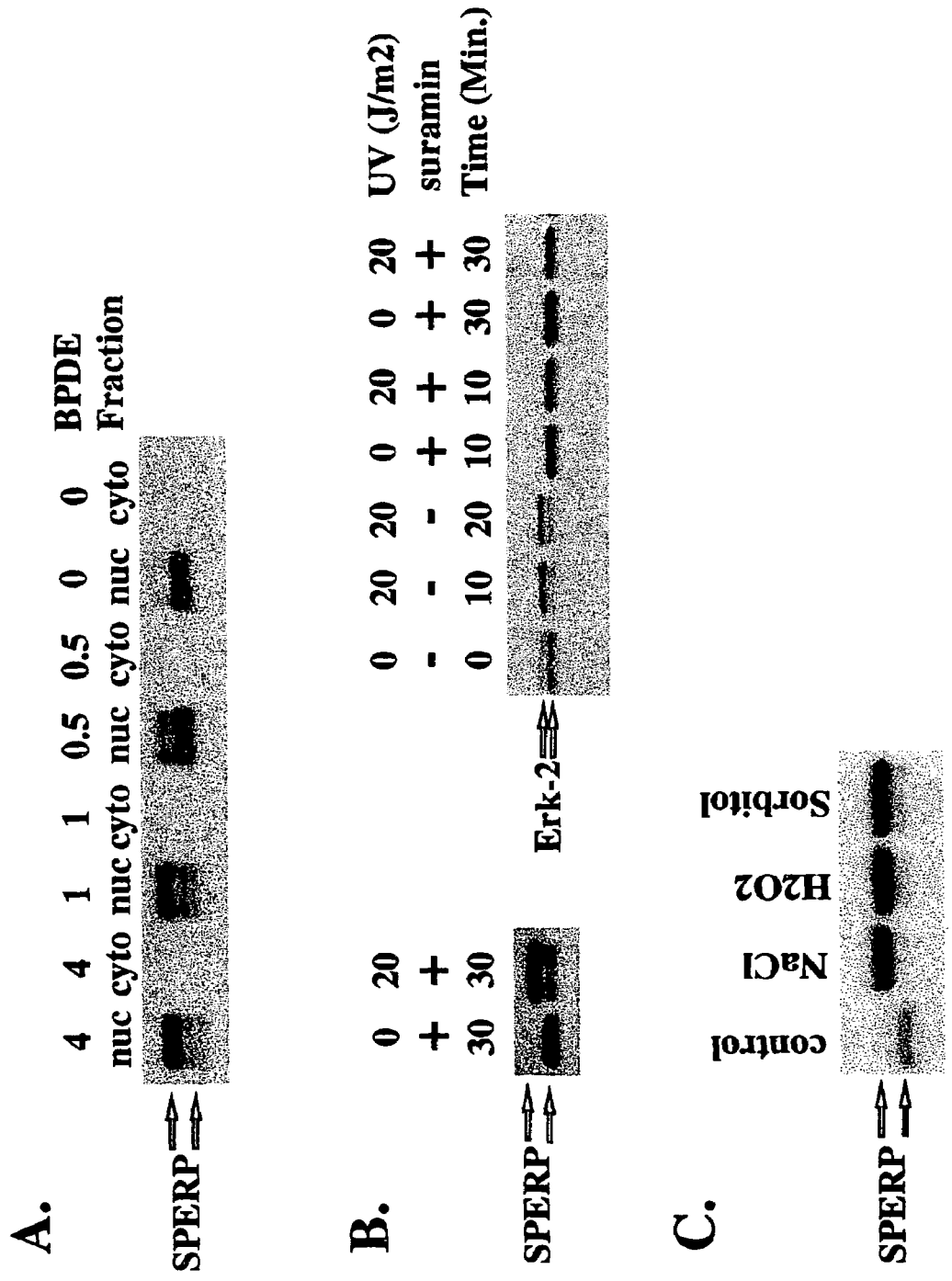
FIG. 4.

The data shown in FIG. 4 were obtained as follows. (A) IMR90 cells were treated with 0, 0.5, 1, or 4 µM of BPDE and trypsinized after 30 minutes. Digitonin-solubilized fraction (Cyto) and NP-40-solubilized fraction (Nuc) were separated on SDS-PAGE. SC-54 was used for Western Blotting. In FIG. 4, (B) IMR90 cells were incubated in the presence or absence of suramin (0.15 mM) for 1 hour before being irradiated with 0 or 20 J/m$^2$ of UVC. After 0, 10, 20 or 30 minutes, whole cell lysates were prepared, separated on SDS-PAGE and transferred to a PVDF membrane. SC-54 or an antibody against human ERK2 was used for Western Blotting. Nogo B and ERK2 were shown by arrows. In FIG. 4, (C) IMR90 cells were treated with 0.7 M NaCl, 1 mM H$_2$O$_2$, 0.4 M Sorbitol or PBS (control) for 45 minutes before being lysed. Whole cell lysates were separated on SDS-PAGE. SC-54 was used for Western Blotting.

EXAMPLE 2

P38 MAPK Activation led to the P46 Hyperphosphorylation

Figure 5:
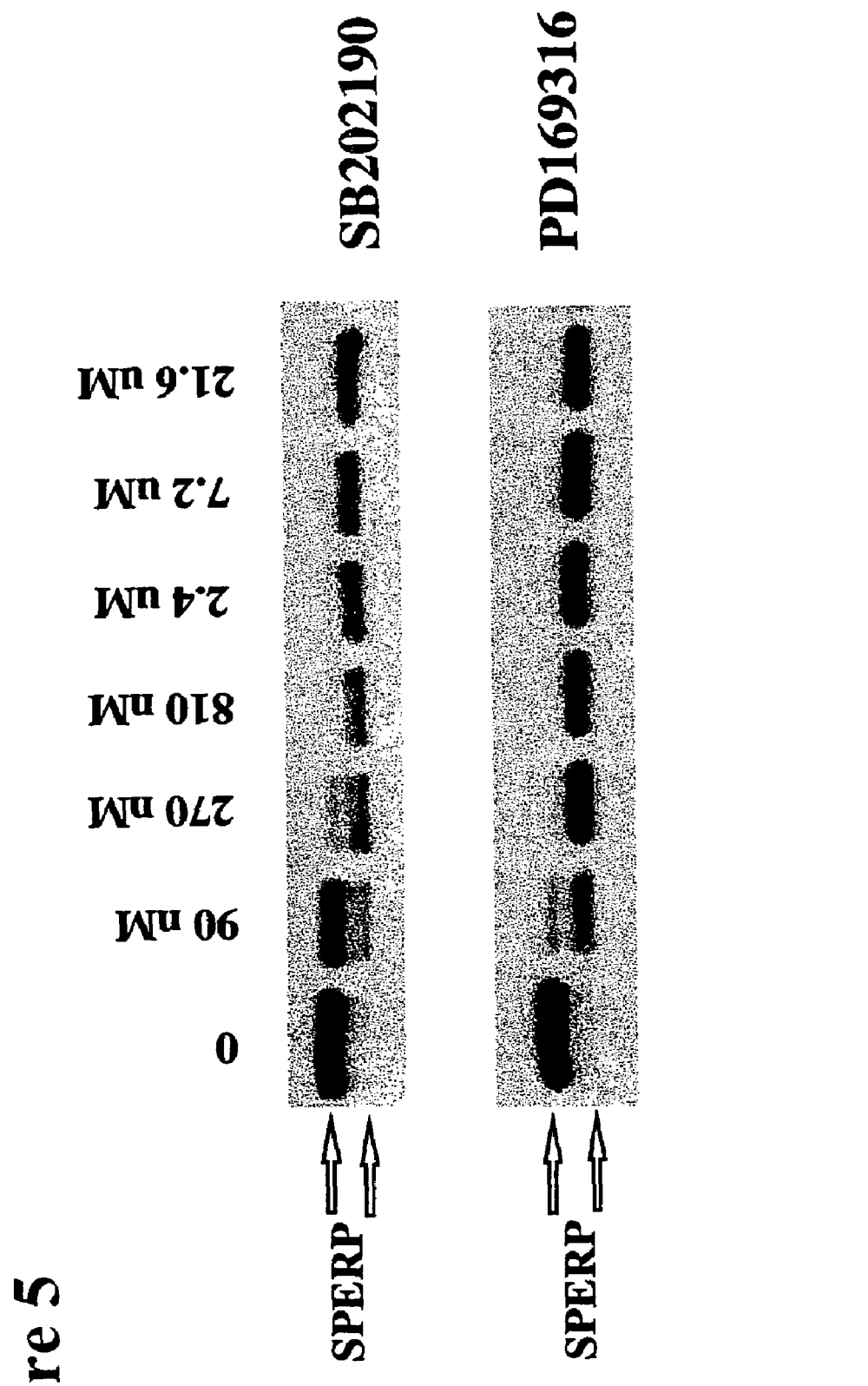
FIG. 5.

It has been shown that elevated cellular stress level can activate p38 MAPK. The role of activation of p38 MAPK in p46 hyperphosphorylation was investigated. As shown in FIG. 5, p46 hyperphosphorylation was almost completely abolished in the presence of 270 nM of the p38-specific inhibitor SB202190 (IC50=300 nM) or in the presence of 90 nM of another p38-specific inhibitor PD169316 (IC50=89 nM). Another p38-specific inhibitor, SB203580, also showed similar effects. The control compound, SB202474, had no effect. The p46 hyperphosphorylation was not affected by the presence of 50 nM of wortmannin (IC50 for PI-3 kinase: 5 nM) or 20 uM of PD98059 (IC50 for MEK: 2 uM). It was concluded that p46 hyperphosphorylation was a result of p38 activation.

EXAMPLE 3

Identification of P46 as a Novel Protein

The present observation that p46 could be completely released by NP-40 but not by digitonin (FIG. 7B) strongly suggested that p46 was localized in the nucleus or organelles. To purify the protein, proteins were with NP-40 and passed through a Mono-S column followed by a Mono-Q column, using Western Blot as the indicator (FIGS. 6A and 6B). When the fractions eluted from the Mono-Q column on SDS-PAGE were separated and the gel stained with Coomassie Blue, there were only 4 bands visible at around 46 KD: a fast migrating doublet and a much weaker, slow migrating doublet (FIG. 6C), which was expected as the proteins were extracted from asynchronously growing cells. These proteins were purified from the SDS polyacrylamide gel and analyzed with Mass Spectrometry. The mass for the intact p46 was determined as 40523 (±200) daltons, suggesting that it is a novel protein. This was confirmed by further analysis using nanospray technique, which identified four novel sequence tags.

The purified p46 was also subjected to microsequencing and three peptide sequences were generated. These sequences were used to identify a putative full-length open reading frame, encoding a protein of 373 amino acids (FIG. 5A). The translated sequence contained all 4 sequence tags identified by Mass Spectrometry and three peptide sequences, indicating that this was the p46 gene.

The data shown in FIG. 6 were obtained as follows. In FIG. 6A, exponentially growing IMR90 cells were lysed by digitonin followed by NP-40 as described in Example 1. Only the NP-40-solubilized fraction was subjected to purification by Mono-S column. Eluted fractions were separated on SDS-PAGE. SC-54 was used for Western Blotting. Positions of Nogo B and the 46 KD protein marker were shown. Fraction numbers were indicated. In FIG. 6B, eluted fractions 42–48 from the Mono-S column were combined and subjected to purification by Mono-Q column. Eluted fractions were separated on SDS-PAGE. SC-54 was used for Western Blotting. Positions of Nogo B and the 46 KD protein marker were shown. Fraction numbers were indicated. In FIG. 6C, eluted fractions from Mono-Q column were separated on SDS-PAGE. The gel was then stained with Coomassie Bright Blue. Sizes of the molecular weight markers were shown. BSA was loaded as an indicator of size and amount of protein.

EXAMPLE 4

P46 is Localized to Endoplasmic Reticulum

The C terminus of p46, i.e., amino acid 188-amino acid 373, is highly homologous to the C terminus of the human neuroendocrine-specific proteins (NSPs) (FIG. 1B), while its N terminus (amino acid 1-amino acid 187) shares little homology to any known proteins. NPs have been localized to endoplasmic reticulum (ER), and its ER localization signal (KRHAE at the C terminus) is highly conserved in p46 (KRKAE at the C terminus). To determine the subcellular localization of p46, a fragment of the p46 gene was cloned, which covers all coding sequence and almost all 3' untranslated region, into an in-frame position at the 3' end of the green fluorescence protein gene (EGFP). In primary fibroblasts, EGFP equally distributed throughout the cell (FIG. 2A), while EGFP-p46 fusion protein mainly localized in the cytosol as a tubular-reticular-like structure with the strongest fluorescence signal surrounding the nucleus (FIG. 2B), which is a classical feature for ER resident proteins. Similar localization was also observed when this fusion protein was expressed in an SV-40 immortalized human fibroblast cell line (FIGS. 2C and 2D). Western Blot using monoclonal antibody against GFP showed that the free EGFP could be released by digitonin while the EGFP-p46 fusion protein could only be released by NP40, further confirming the change of its localization (FIG. 2E). This was the first ER resident protein found to be phosphorylated as a result of p38 MAPK activation.

FIG. 2 shows the subcellular localization of Nogo B. IMR90 cells (A,B) or GM00637 cells (C,D) were infected with a retrovirus expressing EGFP alone (A) or an EGFP-Nogo B fusion protein (B,C,D). Pictures were taken at 2–3 days after infection. (E). IMR90 cells infected with retrovirus expressing EGFP alone (lanes 1 and 2) or an EGFP-Nogo B fusion protein (lanes 3 and 4) were trypsinized and lysed with digitonin followed by NP-40. Digitonin-solubilized fractions (cyto; lanes 1 and 3) and NP-40-solubilized fractions (nuc; lanes 2 and 4) were separated on SDS-PAGE and transferred to a PVDF membrane. A monoclonal antibody against GFP was used for Western Blotting.

EXAMPLE 5

Tissue Distribution of Nogo B

The Multiple Tissue Northern Blot was probed with the full-length Nogo B gene, and two major transcripts could be detected (FIG. 3A). The longer transcript, which was about 2600 nucleotides in length, was expressed consistently at all tissues with the exception of heart, where the expression level was significantly higher (FIG. 3A). The level of the short transcript, about 2300 nucleotides in length, was the highest in the skeletal muscle, followed by brain and liver (FIG. 3A). Presence of similar amount of total mRNA in each lane was confirmed by probing the same membrane with a β-actin probe (FIG. 3B).

As discussed above, FIG. 3 shows the tissue-specific expression of the Nogo B gene. In FIG. 3A, a Northern Blot containing mRNA from different tissues was probed with the full-length Nogo B cDNA. Positions of the two major Nogo B transcripts were shown. The position of the 2.4 KB RNA marker was also indicated. In FIG. 3B, the same blot was stripped and reprobed with the cDNA for β-actin. Positions of the actin transcript and the 2.4 KB RNA marker are shown.

EXAMPLE 6

Loss of the Major Nogo B Transcript in Brain Tumors

Figure 8:
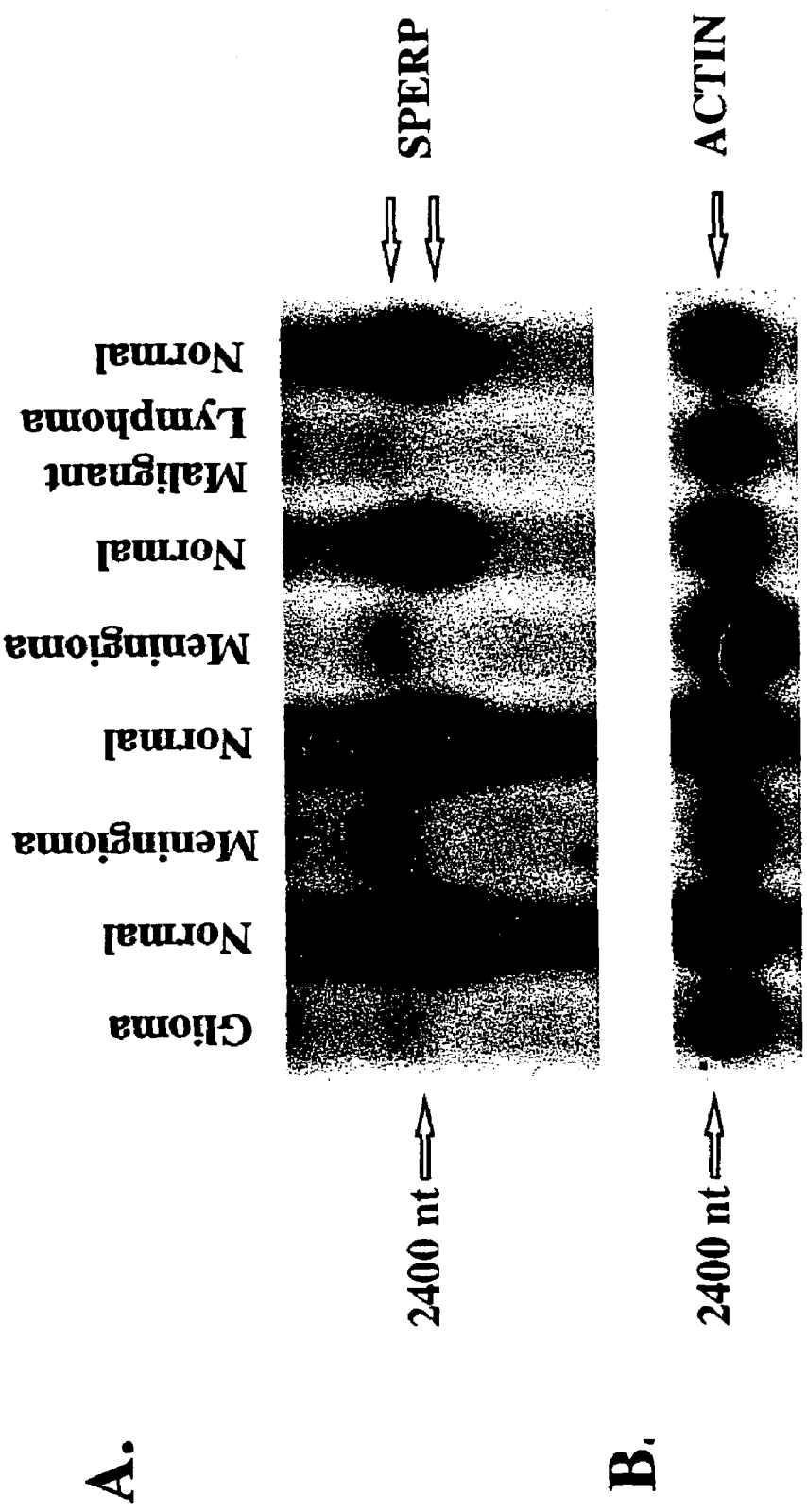
FIG. 8. Loss of the major Nogo transcript in brain tumors. (A). A Northern Blot containing total RNA from different tumor samples and corresponding normal samples (collected from the normal tissue surrounding the tumor) was probed with the full-length Nogo B cDNA. Positions of the two major Nogo transcripts were shown. The position of the 2.4 KB RNA marker was also indicated. (B). The same blot was stripped and reprobed with the cDNA for β-actin. Positions of the actin transcript and the 2.4 KB RNA marker were shown.

To determine whether Nogo B was involved in tumorigenesis, a Brain Tumor Northern Blot was probed with the full-length Nogo B gene. In all four normal brain samples, the short transcript was the major transcript (FIG. 8A), confirming the previous observation (FIG. 3A). However, in the four corresponding tumor samples, the level of the short transcript was too low to be detected; rather, a weak signal for the long transcript was detected (FIG. 8A). This variation was not due to unequal loading because the signal for β-actin was similar in all lanes (FIG. 8B). Furthermore, the locations of the α-actin transcript was almost identical to that of the short transcript of the Nogo B gene, ruling out an artifact or a defective membrane.

EXAMPLE 7

Nogo B is Important for Cell Growth and Viability

During purification of the Nogo B protein, it was identified as an abundant protein because it was about 1/2000 of the NP-40-solublized proteins. To determine whether Nogo B plays a role in normal cell growth, specific antisense oligonucleotides were used to downregulate the level of Nogo B. Four uniformly phosphorothioate modified oligonucleotides, whose sequences were complementary to various regions of the mRNA sequence of the Nogo B gene, were synthesized, and transfected into IMR90 cells using a synthetic lipitoid. A control FITC-labeled oligonucleotide was used in each experiment as an indicator of the transfection efficiency, which was almost 100%. After 16 hours of transfection, slight cytotoxicity was observed for cells transfected with antisense oligonucleotides. After another 24 hours, the cytotoxicity became more obvious (FIG. 9A). There were fewer cells attached to dishes in which cells were transfected with antisense oligonucleotides than those in dishes in which cells were either untransfected or transfected with the FITC-labeled control oligonucleotide (FIG. 9A). This cytotoxicity remained for another 1–2 days before the surviving cells started growing back, suggesting that at that time the antisense oligonucleotides bad been degraded or were no longer functional.

To determine whether transfection of antisense oligonucleotides actually downregulated the levels of Nogo B, protein lysates were prepared from cells remaining attached at 24 hours after completion of transfection. As shown in FIG. 9B, the levels of Nogo B in cells transfected with antisense oligonucleotides were much lower than that in untransfected cells or cells transfected with the control oligonucleotide. As an indicator of slower cell growth, the amount of cdc2, which is synthesized during late S phase and G2 phase, was significantly lower in cells transfected with antisense oligonucleotides (FIG. 9B). This was not due to the effect of morphological changes on ER because levels of another ER resident protein, GRP94, were constant in all samples (FIG. 9C). Therefore the cytotoxic effect observed was very likely to be a specific result of downregulation of Nogo B, suggesting that Nogo B plays an important role in maintaining normal cell growth and viability.

Figure 9:
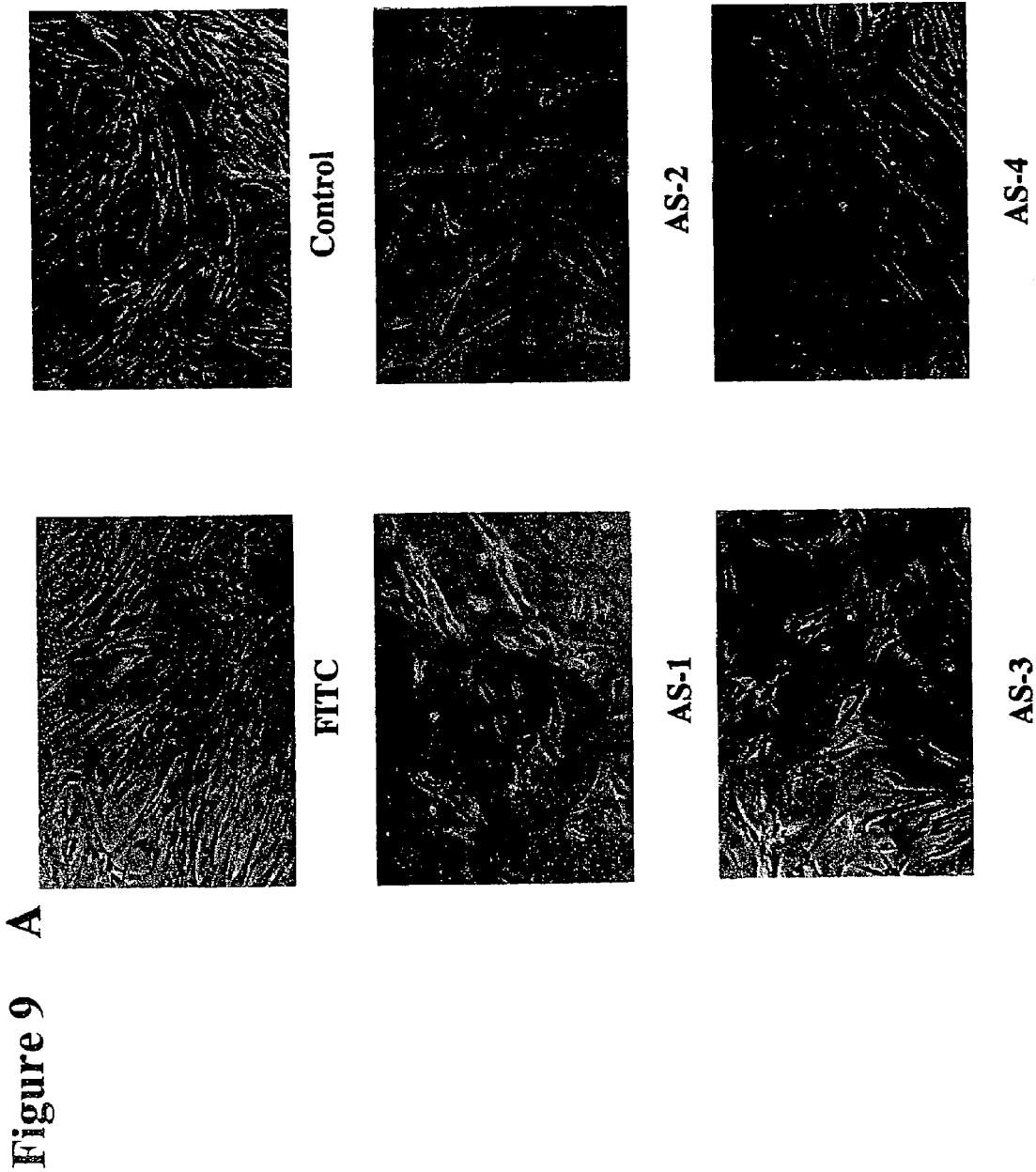
FIG. 9. Specific downregulation of Nogo using antisense oligonucleotides correlated with cytotoxicity and slowed cell growth. (A) IMR90 cells were plated at 3×10$^5$ cells per 60 mm dish. After 24 hours, cells were transfected with antisense oligonucleotides or PBS (control) for 16 hours. Cells were then incubated in normal medium for another 24 hours. Photographs illustrate areas representative of the state of cell growth on the dish. (B) Cells were trypsinized, then lysed. Lysates were separated on SDS-PAGE and transferred to a PVDF membrane, and the membrane was cut into half. The half containing proteins with lower molecular weight was probed with SC-54. Positions of Nogo and Cdc2 are shown. (C) The remaining half of the membrane containing proteins with higher molecular weight was probed with a polyclonal antibody against GRP94.
Figure 9:
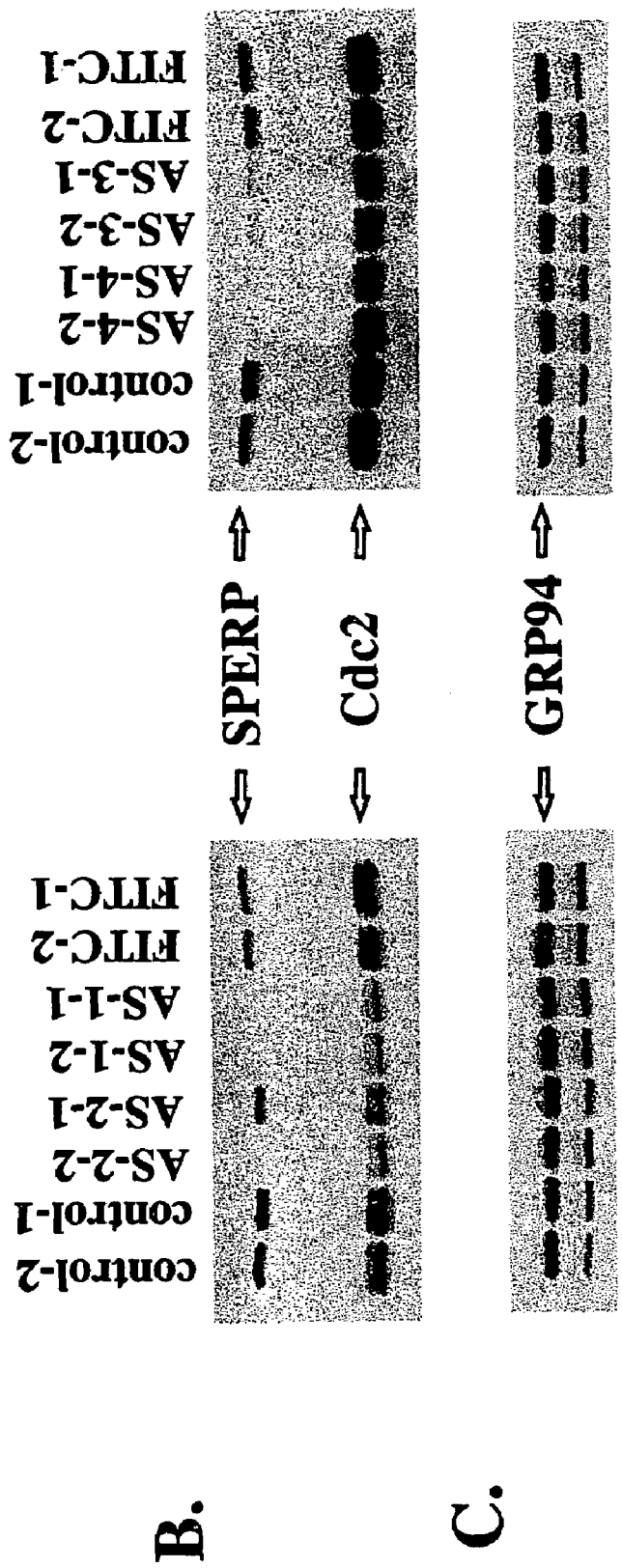

As indicated above, FIG. 9 shows that specific downregulation of Nogo B using antisense oligonucleotides correlated with cytotoxicity and slowed cell growth. In FIG. 9A, IMR90 cells were plated at $3 \times 10^5$ cells per 60 mm dish. After 24 hours, cells were transfected with various antisense oligonucleotides or just PBS (control) for 16 hours. Cells were then incubated in normal medium for another 24 hours. Pictures were taken for areas representative of the state of cell growth on the dish. Cells were trypsinized and counted. For this typical experiment, the number of the remaining cells per dish were as follows: Control-1, $47 \times 10^5$; Control-2, $48 \times 10^5$; FITC-1, $40 \times 10^5$; FITC-2, $37 \times 10^5$; AS-1-1, $25 \times 10^5$; AS-1-2, $27 \times 10^5$; AS-2-1, $35 \times 10^5$; AS-2-2, $30 \times 10^5$; AS-3-1, $27 \times 10^5$; AS-3-2, $30 \times 10^5$; AS-4-1, $35 \times 10^5$; AS-4-2, $30 \times 10^5$. In FIG. 9B, the trypsinized cells were then lysed. Lysates were separated on SDS-PAGE and transferred to a PVDF membrane. The membrane was cut in half. The half containing proteins with lower molecular weight was probed with SC-54. Positions of Nogo B and Cdc2 were shown. In FIG. 9C, the other half of the membrane containing proteins with higher molecular weight was probed with a polyclonal antibody against GRP94.

The following material has been deposited at the ATCC, 10801 University Boulevard, Manassas, Va. 20110-2209:

| Material | Date of Deposit | CMCC Number | ATCC Accession No. |
|---|---|---|---|
| Plasmid pBluescript-SK(+) | May 19, 1999 | 4965 | PTA-89 |

This deposit is provided merely as convenience to those of skill in the art, and is not an admission that a deposit is required under 35 U.S.C. § 112. The sequence of the polynucleotides contained within the deposited material, as well as the amino acid sequence of the polypeptides encoded thereby, are incorporated herein by reference and are controlling in the event of any conflict with the written description of sequences herein. A license may be required to make, use, or sell the deposited material, and no such license is granted hereby.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. An isolated nucleic acid molecule comprising of a polynucleotide selected from the group consisting of:

(a) a polynucleotide encoding the amino acids from 1 to 373 of SEQ ID NO:2;

(b) a polynucleotide encoding the amino acids from 2 to 373 of SEQ ID NO:2;

(c) a polynucleotide encoding the amino acids from 1 to 197 and 236 to 373 of SEQ ID NO:2, wherein said amino acids 197 and 236 are joined by a peptide bond;

(d) a polynucleotide encoding the amino acids from 1 to 288 and 336 to 373 of SEQ ID NO:2; wherein amino acids and 288 and 336 are joined by a peptide bond;

(e) a polynucleotide encoding the amino acids from 1 to 197, amino acids 236 to 288, and amino acids 336 to 373 of SEQ ID NO:2, wherein said amino acids 197 and 236 are joined by a peptide bond, and said amino acids and 288 and 336 are joined by a peptide bond;
(f) a polynucleotide encoding the amino acids from 1 to 187 of SEQ ID NO:2;
(g) a polynucleotide encoding the amino acids from 2 to 187 of SEQ ID NO:2;
(h) a polynucleotide encoding the amino acids from 1 to 198 of SEQ ID NO:2;
(j) the polynucleotide deposited as ATCC Accession No. PTA 89; and
(j) the polynucleotide complement of the polynucleotide of any one of the polynucleotides of (a)–(i).

2. An isolated nucleic acid molecule comprising at least 700 contiguous nucleotides from the coding region of SEQ ID NO:1, wherein said coding region encodes SEQ ID NO:2.

3. A method of making a recombinant vector comprising inserting a nucleic acid molecule of claim 1 into a vector in operable linkage to a promoter.

4. A recombinant vector produced by the method of claim 3.

5. A method of making a recombinant host cell comprising introducing the recombinant vector of claim 4 into said host cell.

6. A recombinant host cell produced by the method of claim 5.

7. A recombinant method of producing a polypeptide, comprising culturing the recombinant host cell of claim 6 under conditions such that said polypeptide is expressed and recovering said polypeptide.

8. A method of inhibiting cell growth in vitro, said method comprising transfecting said cell with a polynucleotide, wherein said polynucleotide is between 8 and 50 nucleotides in length and said polynucleotide between 8 and 50 nucleotides is complementary to a mRNA molecule encoding SEQ ID NO:2, wherein said polynucleotide is specific to Nogo B cDNA.

9. The method of claim 8, wherein said polynucleotide is between about 15 and 25 nucleotides in length.

10. The method of claim 8, wherein said polynucleotide is selected from the group consisting of SEQ ID NO:4, SEQ ID NO:5 and SEQ ID NO:6.

11. A method of making a recombinant vector comprising inserting the nucleic acid molecule of claim 2 into a vector in operable linkage to a promoter.

12. A recombinant vector produced by the method of claim 11.

13. A method of making a recombinant host cell comprising introducing the recombinant vector of claim 12 into a host cell.

14. A recombinant host cell produced by the method of claim 13.

15. A recombinant method of producing a polypeptide, comprising culturing the recombinant host cell of claim 14 under conditions such that said polypeptide is expressed and recovering said polypeptide.

* * * * *

SEQUENCE LISTING

<160> NUMBER OF SEQ ID NOS: 11

<210> SEQ ID NO 1
<211> LENGTH: 2240
<212> TYPE: DNA
<213> ORGANISM: Homo sapiens

<400> SEQUENCE: 1

| | | | | | |
|---|---|---|---|---|---|
| cgtcaccaca | gtaggtccct | cggctcagtc | ggcccagccc | ctctcagtcc | tccccaaccc | 60 |
| ccacaaccgc | ccgcggctct | gagacgcggc | cccggcggcg | gcggcagcag | ctgcagcatc | 120 |
| atctccaccc | tccagccatg | gaagacctgg | accagtctcc | tctggtctcg | tcctcggaca | 180 |
| gcccacccg | gccgcagccc | gcgttcaagt | accagttcgt | gagggagccc | gaggacgagg | 240 |
| aggaagaaga | ggaggaggaa | gaggaggacg | aggacgaaga | cctggaggag | ctggaggtgc | 300 |
| tggagaggaa | gcccgccgcc | gggctgtccg | cggcccagt | gcccaccgcc | cctgccgccg | 360 |
| gcgcgcccct | gatggacttc | ggaaatgact | tcgtgccgcc | ggcgccccgg | ggacccctgc | 420 |
| cggccgctcc | ccccgtcgcc | ccggagcggc | agccgtcttg | gacccgagc | ccggtgtcgt | 480 |
| cgaccgtgcc | cgcgccatcc | ccgctgtctg | ctgccgcagt | ctcgccctcc | aagctccctg | 540 |
| aggacgacga | gcctccggcc | cggcctcccc | ctcctccccc | ggccagcgtg | agcccccagg | 600 |
| cagagcccgt | gtggaccccg | ccagccccgg | ctcccgccgc | gccccctcc | accccggccg | 660 |
| cgcccaagcg | caggggctcc | tcgggctcag | tggttgttga | cctcctgtac | tggagagaca | 720 |
| ttaagaagac | tggagtggtg | tttggtgcca | gcctattcct | gctgctttca | ttgacagtat | 780 |
| tcagcattgt | gagcgtaaca | gcctacattg | ccttggccct | gctctctgtg | accatcagct | 840 |
| ttaggatata | caagggtgtg | atccaagcta | tccagaaatc | agatgaaggc | cacccattca | 900 |
| gggcatatct | ggaatctgaa | gttgctatat | ctgaggagtt | ggttcagaag | tacagtaatt | 960 |
| ctgctcttgg | tcatgtgaac | tgcacgataa | aggaactcag | gcgcctcttc | ttagttgatg | 1020 |
| atttagttga | ttctctgaag | tttgcagtgt | tgatgtgggt | atttacctat | gttggtgcct | 1080 |
| tgtttaatgg | tctgacacta | ctgattttgg | ctctcatttc | actcttcagt | gttcctgtta | 1140 |
| tttatgaacg | gcatcaggca | cagatagatc | attatctagg | acttgcaaat | aagaatgtta | 1200 |
| aagatgctat | ggctaaaatc | caagcaaaaa | tccctggatt | gaagcgcaaa | gctgaatgaa | 1260 |
| aacgcccaaa | ataattagta | ggagttcatc | tttaaagggg | atattcattt | gattatacgg | 1320 |
| gggagggtca | gggaagaacg | aaccttgacg | ttgcagtgca | gtttcacaga | tcgttgttag | 1380 |
| atctttattt | ttagccatgc | actgttgtga | ggaaaaatta | cctgtcttga | ctgccatgtg | 1440 |
| ttcatcatct | taagtattgt | aagctgctat | gtatggattt | aaaccgtaat | catatctttt | 1500 |
| tcctatctga | ggcactggtg | gaataaaaaa | cctgtatatt | ttactttgtt | gcagatagtc | 1560 |
| ttgccgcatc | ttggcaagtt | gcagagatgg | tggagctaga | aaaaaaaaaa | aaaagcccct | 1620 |
| tttcagtttg | tgcactgtgt | atggtccgtg | tagattgatg | cagattttct | gaaatgaaat | 1680 |
| gtttgtttag | acgagatcat | accggtaaag | caggaatgac | aaagcttgct | tttctggtat | 1740 |
| gttctaggtg | tattgtgact | tttactgtta | tattaattgc | caatataagt | aaatatagat | 1800 |
| tatatatgta | tagtgtttca | caaagcttag | acctttacct | tccagccacc | ccacagtgct | 1860 |
| tgatatttca | gagtcagtca | ttggttatac | atgtgtagtt | ccaaagcaca | taagctagaa | 1920 |
| gaagaaaatat | ttctaggagc | actaccatct | gttttcaaca | tgaaatgcca | cacacataga | 1980 |
| actccaacaa | catcaatttc | attgcacaga | ctgactgtag | ttaattttgt | cacagaatct | 2040 |

-continued

```
atggactgaa tctaatgctt ccaaaaatgt tgtttgtttg caaatatcaa acattgttat    2100
gcaagaaatt attaattaca aaatgaagat ttataccatt gtggtttaag ctgtactgaa    2160
ctaaatctgt ggaatgcatt gtgaactgta aaagcaaagt atcaataaag cttatagact    2220
taaaaaaaaa aaaaaaaaa                                                 2240
```

<210> SEQ ID NO 2
<211> LENGTH: 373
<212> TYPE: PRT
<213> ORGANISM: Homo sapien

<400> SEQUENCE: 2

| Met | Glu | Asp | Leu | Asp | Gln | Ser | Pro | Leu | Val | Ser | Ser | Asp | Ser | Pro |
|---|---|---|---|---|---|---|---|---|---|---|---|---|---|---|
| 1 | | | | 5 | | | | | 10 | | | | | 15 |

| Pro | Arg | Pro | Gln | Pro | Ala | Phe | Lys | Tyr | Gln | Phe | Val | Arg | Glu | Pro | Glu |
|---|---|---|---|---|---|---|---|---|---|---|---|---|---|---|---|
| | | | 20 | | | | | 25 | | | | | 30 | | |

Asp Glu Glu Glu Glu Glu Glu Glu Glu Asp Glu Asp Glu Asp
            35                  40                  45

Leu Glu Glu Leu Glu Val Leu Glu Arg Lys Pro Ala Ala Gly Leu Ser
 50                  55                  60

Ala Ala Pro Val Pro Thr Ala Pro Ala Ala Gly Ala Pro Leu Met Asp
 65                  70                  75                  80

Phe Gly Asn Asp Phe Val Pro Pro Ala Pro Arg Gly Phe Leu Pro Ala
                 85                  90                  95

Ala Pro Pro Val Ala Pro Glu Arg Gln Pro Ser Trp Asp Pro Ser Pro
                100                 105                 110

Val Ser Ser Thr Val Pro Ala Pro Ser Phe Leu Ser Ala Ala Ala Val
                115                 120                 125

Ser Pro Ser Lys Leu Pro Glu Asp Asp Glu Pro Pro Ala Arg Pro Pro
130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
                165                 170                 175

Lys Arg Arg Gly Ser Ser Gly Ser Val Val Val Asp Leu Leu Tyr Trp
                180                 185                 190

Arg Asp Ile Lys Lys Thr Gly Val Val Phe Gly Ala Ser Leu Phe Leu
                195                 200                 205

Leu Leu Ser Leu Thr Val Phe Ser Ile Val Ser Val Thr Ala Tyr Ile
                210                 215                 220

Ala Leu Ala Leu Leu Ser Val Thr Ile Ser Pro Arg Ile Tyr Lys Gly
225                 230                 235                 240

Val Ile Gln Ala Ile Gln Lys Ser Asp Glu Gly His Pro Phe Arg Ala
                245                 250                 255

Tyr Leu Glu Ser Glu Val Ala Ile Ser Glu Glu Leu Val Gln Lys Tyr
                260                 265                 270

Ser Asn Ser Ala Leu Gly His Val Asn Cys Thr Ile Lys Glu Leu Arg
                275                 280                 285

Arg Leu Phe Leu Val Asp Asp Leu Val Asp Ser Leu Lys Phe Ala Val
                290                 295                 300

Leu Met Trp Val Phe Thr Tyr Val Gly Ala Leu Phe Asn Gly Leu Thr
305                 310                 315                 320

Leu Leu Ile Leu Ala Leu Ile Ser Leu Phe Ser Val Pro Val Ile Tyr
                325                 330                 335

-continued

```
Glu Arg His Gln Ala Gln Ile Asp His Tyr Leu Gly Leu Ala Asn Lys
            340                 345                 350

Asn Val Lys Asp Ala Met Ala Lys Ile Gln Ala Lys Ile Pro Gly Leu
        355                 360                 365

Lys Arg Lys Ala Glu
    370

<210> SEQ ID NO 3
<211> LENGTH: 25
<212> TYPE: RNA
<213> ORGANISM: Artificial Sequence
<220> FEATURE:
<223> OTHER INFORMATION: Antisense oligonucleotide

<400> SEQUENCE: 3
cuggauagcu uggaucacac ccuug                                         25

<210> SEQ ID NO 4
<211> LENGTH: 25
<212> TYPE: RNA
<213> ORGANISM: Artificial Sequence
<220> FEATURE:
<223> OTHER INFORMATION: Antisense oligonucleotide

<400> SEQUENCE: 4
caacuucagg auuccagaua ugccc                                         25

<210> SEQ ID NO 5
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 5
auuccaccag ugccucagau agga                                          24

<210> SEQ ID NO 6
<211> LENGTH: 24
<212> TYPE: RNA
<213> ORGANISM: Artificial Sequence
<220> FEATURE:
<223> OTHER INFORMATION: Antisense oligonucleotide

<400> SEQUENCE: 6
augaucuauc ugugccugau gccg                                          24

<210> SEQ ID NO 7
<211> LENGTH: 356
<212> TYPE: PRT
<213> ORGANISM: Homo sapiens

<400> SEQUENCE: 7

Met Ala Ala Glu Asp Ala Leu Pro Ser Gly Tyr Val Ser Phe Gly His
 1               5                  10                  15

Val Gly Gly Pro Pro Ser Pro Ala Ser Pro Ser Ile Gln Tyr Ser
            20                  25                  30

Ile Leu Arg Glu Glu Arg Glu Ala Glu Leu Asp Ser Glu Leu Ile Ile
        35                  40                  45

Glu Ser Cys Asp Ala Ser Ser Ala Ser Glu Glu Ser Pro Lys Arg Glu
    50                  55                  60

Gln Asp Ser Pro Pro Met Lys Pro Ser Ala Leu Asp Ala Ile Arg Glu
```

```
                65                  70                  75                  80
Glu Thr Gly Val Arg Ala Glu Arg Ala Pro Ser Arg Arg Gly Leu
                    85                  90                  95
Ala Glu Pro Gly Ser Phe Leu Asp Tyr Pro Ser Thr Glu Pro Gln Pro
                100                 105                 110
Gly Pro Glu Leu Pro Pro Gly Asp Gly Ala Leu Glu Pro Glu Thr Pro
                115                 120                 125
Met Leu Pro Arg Lys Pro Glu Glu Asp Ser Ser Asn Gln Ser Pro
        130                 135                 140
Ala Ala Thr Lys Gly Pro Gly Pro Leu Pro Gly Ala Pro Pro
145                 150                 155                 160
Leu Leu Phe Leu Asn Lys Gln Lys Ala Ile Asp Leu Leu Tyr Trp Arg
                165                 170                 175
Asp Ile Lys Gln Thr Gly Ile Val Phe Gly Ser Phe Leu Leu Leu
                180                 185                 190
Phe Ser Leu Thr Gln Phe Ser Val Ser Val Val Ala Tyr Leu Ala
            195                 200                 205
Leu Ala Ala Leu Ser Ala Thr Ile Ser Phe Arg Ile Tyr Lys Ser Val
            210                 215                 220
Leu Gln Ala Val Gln Lys Thr Asp Glu Gly His Pro Phe Lys Ala Tyr
225                 230                 235                 240
Leu Glu Leu Glu Ile Thr Leu Ser Gln Glu Gln Ile Gln Lys Tyr Thr
                245                 250                 255
Asp Cys Leu Gln Phe Tyr Val Asn Ser Thr Leu Lys Glu Leu Arg Arg
                260                 265                 270
Leu Phe Leu Val Gln Asp Leu Val Asp Ser Leu Lys Phe Ala Val Leu
            275                 280                 285
Met Trp Leu Leu Thr Tyr Val Gly Ala Leu Phe Asn Gly Leu Thr Leu
        290                 295                 300
Leu Leu Met Ala Val Val Ser Met Phe Thr Leu Pro Val Val Tyr Val
305                 310                 315                 320
Lys His Gln Ala Gln Ile Asp Gln Tyr Leu Gly Leu Val Arg Thr His
                325                 330                 335
Ile Asn Ala Val Val Ala Lys Ile Gln Ala Lys Ile Pro Gly Ala Lys
                340                 345                 350
Arg His Ala Glu
        355

<210> SEQ ID NO 8
<211> LENGTH: 371
<212> TYPE: PRT
<213> ORGANISM: Homo sapiens

<400> SEQUENCE: 8

Met Glu Asp Leu Asp Gln Ser Pro Leu Val Ser Ser Asp Ser Pro
1               5                   10                  15
Pro Arg Pro Gln Pro Ala Phe Lys Tyr Gln Phe Val Arg Glu Pro Glu
                20                  25                  30
Asp Glu Glu Glu Glu Glu Glu Glu Glu Glu Asp Glu Asp Glu Asp
            35                  40                  45
Leu Glu Glu Leu Glu Val Leu Glu Arg Lys Pro Ala Ala Gly Leu Ser
        50                  55                  60
Ala Ala Pro Val Pro Thr Ala Pro Ala Ala Gly Ala Pro Leu Met Asp
65                  70                  75                  80
```

```
Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
           100                 105                 110

Val Ser Ser Thr Val Pro Ala Pro Ser Pro Leu Ser Ala Ala Ala Val
           115                 120                 125

Ser Pro Ser Lys Leu Pro Glu Asp Asp Glu Pro Pro Ala Arg Pro Pro
    130                 135                 140

Pro Pro Pro Pro Ala Ser Val Ser Pro Gln Ala Glu Pro Val Trp Thr
145                 150                 155                 160

Pro Pro Ala Pro Ala Pro Ala Pro Pro Ser Thr Pro Ala Ala Pro
               165                 170                 175

Lys Arg Arg Gly Ser Ser Gly Ser Val Val Asp Leu Leu Tyr Trp
               180                 185                 190

Arg Asp Ile Lys Lys Thr Gly Val Val Phe Gly Ala Ser Leu Phe Leu
           195                 200                 205

Leu Leu Ser Leu Thr Val Phe Ser Ile Val Ser Val Thr Ala Tyr Ile
    210                 215                 220

Ala Leu Ala Leu Leu Ser Val Thr Ile Ser Phe Arg Ile Tyr Lys Gly
225                 230                 235                 240

Val Ile Gln Ala Ile Gln Lys Ser Asp Glu Gly His Pro Phe Arg Ala
               245                 250                 255

Tyr Leu Glu Ser Glu Val Ala Ile Ser Glu Glu Leu Val Gln Lys Tyr
           260                 265                 270

Ser Asn Ser Ala Leu Gly His Val Asn Cys Thr Ile Lys Glu Leu Arg
       275                 280                 285

Arg Leu Phe Leu Val Asp Asp Leu Val Asp Ser Leu Lys Phe Ala Val
    290                 295                 300

Leu Met Trp Val Phe Thr Tyr Val Gly Ala Leu Phe Asn Gly Leu Thr
305                 310                 315                 320

Leu Leu Ile Leu Ala Leu Ile Ser Leu Phe Ser Val Pro Val Ile Tyr
               325                 330                 335

Glu Arg His Gln Ala Gln Ile Asp His Tyr Leu Gly Leu Ala Asn Lys
               340                 345                 350

Asn Val Lys Asp Ala Met Ala Lys Ile Gln Ala Lys Ile Pro Gly Leu
           355                 360                 365

Lys Arg Lys
        370

<210> SEQ ID NO 9
<211> LENGTH: 205
<212> TYPE: PRT
<213> ORGANISM: Homo sapiens

<400> SEQUENCE: 9

Leu Leu Thr Val Leu Ser Leu Leu Pro Phe Ile Leu Ile Met Met Thr
  1               5                  10                  15

Ser Phe Leu Lys Ile Ser Ile Val Leu Ser Leu Leu Arg Asn Ala Leu
               20                  25                  30

Gly Val Gln Gln Val Pro Pro Asn Met Val Leu Tyr Gly Leu Ala Leu
           35                  40                  45

Phe Leu Thr Leu Phe Val Met Ala Pro Val Phe Glu Glu Ile Tyr Asp
    50                  55                  60

Arg Ala His Gln Pro Leu Leu Asp Ala Leu Ser Asn Ile Ile Ser Leu
65                  70                  75                  80
```

```
Gln Glu Ala Leu Asp Lys Gly Leu Pro Leu Arg Glu Phe Met Leu
                85                  90                  95

Lys His Thr Asp Glu Lys His Glu Leu Ala Leu Phe Met Arg Ser Ala
            100                 105                 110

Arg Glu Glu Arg Leu Trp Pro Lys Glu Met Lys Ala Ala Thr Leu Glu
            115                 120                 125

Lys Asp Asp Leu Leu Val Leu Ile Pro Ala Phe Val Leu Ser Glu Leu
            130                 135                 140

Lys Arg Ala Phe Glu Ile Gly Phe Leu Ile Tyr Leu Pro Phe Ile Val
145                 150                 155                 160

Ile Asp Leu Val Val Ala Ser Ile Leu Met Ala Met Gly Met Met Met
                165                 170                 175

Val Pro Pro Val Thr Ile Ser Leu Pro Phe Lys Leu Leu Leu Phe Val
                180                 185                 190

Leu Val Asp Gly Trp Thr Leu Leu Leu Gly Gly Leu Val
                195                 200                 205

<210> SEQ ID NO 10
<211> LENGTH: 122
<212> TYPE: PRT
<213> ORGANISM: Homo sapiens

<400> SEQUENCE: 10

Leu Phe Leu Leu Leu Ser Leu Thr Val Phe Ser Ile Val Ser Val Thr
 1               5                  10                  15

Ala Tyr Ile Ala Leu Ala Leu Leu Ser Val Thr Ile Ser Phe Arg Ile
                20                  25                  30

Tyr Lys Gly Val Ile Gln Ala Ile Gln Lys Ser Asp Glu Gly His Pro
            35                  40                  45

Phe Arg Ala Tyr Leu Glu Ser Glu Val Ala Ile Ser Glu Glu Leu Val
        50                  55                  60

Gln Lys Tyr Ser Asn Ser Ala Leu Gly His Val Asn Cys Thr Ile Lys
65                  70                  75                  80

Glu Leu Arg Arg Leu Phe Leu Val Asp Asp Leu Val Asp Ser Leu Lys
                85                  90                  95

Phe Ala Val Leu Met Trp Val Phe Thr Tyr Val Gly Ala Leu Phe Asn
            100                 105                 110

Gly Leu Thr Leu Leu Ile Leu Ala Leu Ile
        115                 120

<210> SEQ ID NO 11
<211> LENGTH: 5
<212> TYPE: PRT
<213> ORGANISM: Homo sapiens

<400> SEQUENCE: 11

Lys Arg Tyr Ala Glu
 1               5
```